United States Patent
Maruyama

(10) Patent No.: US 11,747,725 B2
(45) Date of Patent: Sep. 5, 2023

(54) RADIATION-SENSITIVE RESIN COMPOSITION AND METHOD FOR FORMING RESIST PATTERN

(71) Applicant: JSR CORPORATION, Tokyo (JP)

(72) Inventor: Ken Maruyama, Tokyo (JP)

(73) Assignee: JSR CORPORATION, Tokyo (JP)

(*) Notice: Subject to any disclaimer, the term of this patent is extended or adjusted under 35 U.S.C. 154(b) by 135 days.

(21) Appl. No.: 15/953,860

(22) Filed: Apr. 16, 2018

(65) Prior Publication Data

US 2018/0299773 A1 Oct. 18, 2018

(30) Foreign Application Priority Data

Apr. 17, 2017 (JP) ................................ 2017-081633
Mar. 23, 2018 (JP) ................................ 2018-056288

(51) Int. Cl.
| | |
|---|---|
| G03F 7/004 | (2006.01) |
| G03F 7/38 | (2006.01) |
| C07C 303/32 | (2006.01) |
| C07C 309/06 | (2006.01) |
| C07C 309/12 | (2006.01) |
| C07C 309/19 | (2006.01) |
| C07C 309/24 | (2006.01) |
| C07C 381/12 | (2006.01) |
| G03F 7/039 | (2006.01) |
| G03F 7/30 | (2006.01) |

(Continued)

(52) U.S. Cl.
CPC .......... *G03F 7/0045* (2013.01); *C07C 303/32* (2013.01); *C07C 309/06* (2013.01); *C07C 309/12* (2013.01); *C07C 309/19* (2013.01); *C07C 309/24* (2013.01); *C07C 381/12* (2013.01); *G03F 7/0046* (2013.01); *G03F 7/0392* (2013.01); *G03F 7/0397* (2013.01); *G03F 7/162* (2013.01); *G03F 7/168* (2013.01); *G03F 7/2006* (2013.01); *G03F 7/2041* (2013.01); *G03F 7/30* (2013.01); *G03F 7/327* (2013.01); *G03F 7/38* (2013.01); *G03F 7/40* (2013.01)

(58) Field of Classification Search
CPC .... G03F 7/0045; G03F 7/0397; G03F 7/0392; G03F 7/38; C07C 303/32; C07C 309/06; C07C 309/12; C07C 309/19; C07C 381/12; C07C 309/24; C08F 220/16; C08F 220/20; C08F 220/30; C08F 220/38; C08F 228/02
USPC .................................................... 430/270.1
See application file for complete search history.

(56) References Cited

U.S. PATENT DOCUMENTS 8,921,029 B2 * 12/2014 Ichikawa ............... G03F 7/0045
430/270.1
2002/0102491 A1 8/2002 Kodama et al.
(Continued)

FOREIGN PATENT DOCUMENTS

| JP | H10-010715 A | 1/1998 |
| JP | 2002-214774 A | 7/2002 |

(Continued)

OTHER PUBLICATIONS

Office Action dated May 14, 2021 in Japanese Patent Application No. 2018-056288 (with English translation), 6 pages.
Dario Goldfarb et al, "EUV chemically amplified resist component distribution and efficiency for stochastic defect control", Proceedings of SPIE, vol. 11326, SPIEDigitalLibrary.org/conference-proceedings-of-spie, 2020, pp. 1132609-1-1132609-15 (plus cover page).

(Continued)

*Primary Examiner* — John S Chu
(74) *Attorney, Agent, or Firm* — Element IP, PLC

(57) ABSTRACT

A radiation-sensitive resin composition includes: a resin including a structure unit having an acid-dissociable group; a radiation-sensitive acid generator; and a solvent. The radiation-sensitive acid generator includes at least two of compounds represented by formulae (1) to (3), provided that the compound represented by formula (1) and the compound represented by formula (3) within the scope of the compound represented by formula (2) are excluded. In the formulae (1) to (3), $R^1$, $R^2$ and $R^3$ are each independently a group having a cyclic structure; $X^{11}$, $X^{12}$, $X^{21}$, $X^{22}$, $X^{31}$ and $X^{32}$ are each independently a hydrogen atom, a fluorine atom, or a fluorinated hydrocarbon group, provided that both $X^{11}$ and $X^{12}$, both $X^{21}$ and $X^{22}$, and both $X^{31}$ and $X^{32}$ are not a hydrogen atom, respectively.

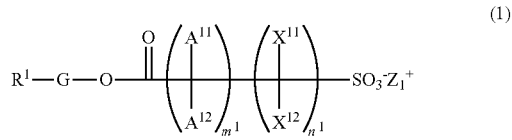

(1)

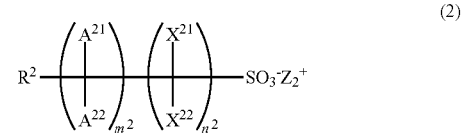

(2)

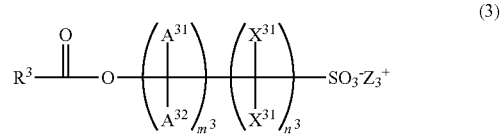

(3)

20 Claims, No Drawings

(51) Int. Cl.
*G03F 7/16* (2006.01)
*G03F 7/40* (2006.01)
*G03F 7/20* (2006.01)
*G03F 7/32* (2006.01)

(56) References Cited

U.S. PATENT DOCUMENTS

| | | | |
|---|---|---|---|
| 2003/0113658 A1 | 6/2003 | Ebata et al. | |
| 2003/0170561 A1 | 9/2003 | Iwasawa et al. | |
| 2010/0035185 A1 | 2/2010 | Hagiwara et al. | |
| 2014/0302438 A1* | 10/2014 | Asano | G03F 7/038 430/281.1 |

FOREIGN PATENT DOCUMENTS

| JP | 2004-002252 A | 1/2004 |
|---|---|---|
| JP | WO 2008/099869 A | 8/2008 |
| JP | 2012193160 A | 10/2012 |
| JP | 2013041245 A | 2/2013 |
| JP | 2013041247 A | 2/2013 |
| JP | 2014029526 A | 2/2014 |
| JP | 2015064494 A | 4/2015 |
| JP | 2015127797 A | 7/2015 |
| JP | 2016210765 A | 12/2016 |
| JP | 2017044929 A | 3/2017 |
| JP | 2018018038 A | 2/2018 |
| WO | WO-2016158711 A1 | 10/2016 |

OTHER PUBLICATIONS

Ping-Jui Wu et al, "Nanoscale inhomogeneity and photoacid generation dynamics in extreme ultraviolet resist materials", Proceedings of SPIE, vol. 10586, SPIEDigitalLibrary.org/conference-proceedings-of-spie, 2018 pp. 105861O-105861O-12 (plus cover page).

Office Action dated Dec. 21, 2021 in Japanese Patent Application No. 2018-056288 (with English translation), 6 pages.

Office Action dated Oct. 1, 2021 in Japanese Patent Application No. 2018-056288 (with English translation), 5 pages.

Office Action dated Mar. 1, 2023 in Japanese Patent Application No. 2022-043285 (with English translation), 7 pages.

* cited by examiner

RADIATION-SENSITIVE RESIN COMPOSITION AND METHOD FOR FORMING RESIST PATTERN

CROSS-REFERENCE TO RELATED APPLICATIONS

The present application claims priority to Japanese Patent Application No. 2017-081633, filed Apr. 17, 2017, and to Japanese Patent Application No. 2018-056288, filed Mar. 23, 2018. The contents of these applications are incorporated herein by reference in their entirety.

BACKGROUND OF THE INVENTION

Field of the Invention

The present invention relates to a radiation-sensitive resin composition and a method for forming a resist pattern.

Description of the Related Art

A photolithography technology using a resist composition has been used for the fine circuit formation in a semiconductor device. As the representative procedure, for example, a resist pattern is formed on a substrate by generating an acid by irradiating the coating of the resist composition with a radioactive ray through a mask pattern, and then reacting in the presence of the acid as a catalyst to generate the difference of solubility of a resin into an alkaline or organic developer between an exposed part and a non-exposed part.

In the photolithography technology, the micronization of the pattern is promoted by using a short wave length radioactive ray such as ArF excimer laser, and by using immersion exposure method (liquid immersion lithography) in which the exposure is carried out in a liquid medium filled in the space between a lens of an exposing apparatus and a resist film. As a next generation technology, a lithography using a short wave length such as an electron beam, X ray and EUV (extreme ultraviolet ray) has been studied.

With progress of the exposing technology, studies of a photoacid generator and the like, a major ingredient of the resist composition, are attempted for the purpose of improving the sensitivity and resolution of the resist composition. As the resist composition having a pattern resolution from micron size to submicron size, proposed is a photosensitive composition including a hydroxystyrene-based polymer having high plasma etching resistance and a photoacid generator having a carbon atom connected to a sulfonate group as a secondary carbon or a tertiary carbon (Patent Document 1). However, in ArF generation, since the absorption of the radioactive ray for exposing in the aromatic structure of the hydroxystyrene-based polymer becomes too strong, it is difficult to form a desired fine shape of pattern. Therefore, there has been used a resin having an alicyclic structure having weak absorption as a protecting group in place of the hydroxystyrene-based polymer. However, the photoacid generator used in combination of the hydroxystyrene-based polymer have no sufficient acid intensity in order to proceed the deprotection of the resin having an alicyclic structure.

Therefore, an acid generator in which a carbon proximal to the sulfonate group is substituted with a fluorine is implemented, as a photoacid generator resulting in an acid having a sufficient acid intensity for the deprotection (Patent Documents 2 to 4).

PRIOR ART DOCUMENT

Patent Document

[Patent Document 1] JP-A-10-10715
[Patent Document 2] JP-A-2002-214774
[Patent Document 3] JP-A-2004-002252
[Patent Document 4] International Patent Publication No. WO 2008/099869

SUMMARY OF THE INVENTION

Problems to be Solved by the Invention

Recently, as the micronization of the resist pattern is proceeding, Critical Dimension Uniformity (CDU) properties which is an index of the uniformity of a line width and a hole diameter, Mask Error Enhancement Factor (MEEF) properties which is an amount of change in the line width and the hole diameter corresponding to the amount of change in a mask size, Line Width Roughness (LWR) properties which shows a variation of the line width of the resist pattern, and the like are required, and various resist properties are required to be further improved. However, in the radiation-sensitive resin composition including the acid generator, all properties are not obtained at a sufficient level.

An object of the present invention is to provide a radiation-sensitive resin composition being capable of providing CDU, MEEF, and LWR properties at sufficient levels even if a next generation exposing technology is applied, and to provide a method for forming a resist pattern.

SUMMARY OF THE INVENTION

As a result of intensive studies for solving these issues, the inventors have found that the object could be accomplished by using a combination of a plurality of acid generators having certain structures, while various resist properties could not be provided by using only one radiation-sensitive acid generator.

The present invention relates to a radiation-sensitive resin composition, including:
a resin including a structure unit having an acid-dissociable group;
a radiation-sensitive acid generator; and
a solvent;
wherein the radiation-sensitive acid generator includes at least two of compounds represented by the following formulae (1) to (3), provided that the compound represented by the formula (1) and the compound represented by the formula (3) within the scope of the compound represented by the formula (2) are excluded:

[Formula 1]

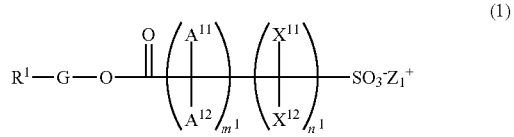

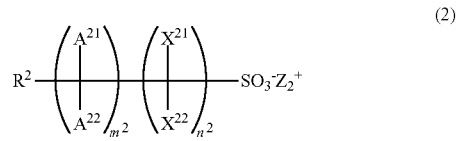

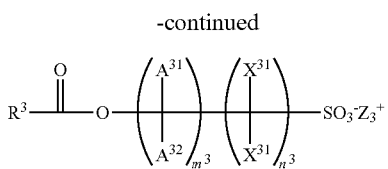

(In the formulae (1) to (3), $R^1$, $R^2$ and $R^3$ are each independently a group having a cyclic structure;

$X^{11}$, $X^{12}$, $X^{21}$, $X^{22}$, $X^{31}$ and $X^{32}$ are each independently a hydrogen atom, a fluorine atom, or a fluorinated hydrocarbon group, provided that both $X^{11}$ and $X^{12}$, both $X^{21}$ and $X^{22}$, and both $X^{31}$ and $X^{32}$ are not a hydrogen atom, respectively;

$A^{11}$, $A^{12}$, $A^{21}$, $A^{22}$, $A^{31}$ and $A^{32}$ are each independently a hydrogen atom, or a hydrocarbon group having a carbon number of 1 to 20;

$m^1$, $m^2$ and $m^3$ are each independently an integer of 0 to 5;

$n^1$, $n^2$ and $n^3$ are each independently an integer of 1 to 4;

G is a single bond, or a divalent linking group; and $Z_1^+$, $Z_2^+$ and $Z_3^+$ are each independently a monovalent onium cation.)

The radiation-sensitive resin composition includes at least two of compounds represented by the above formulae (1) to (3) (hereinafter, also referred respectively as a "compound (1)", for example) as the radiation-sensitive acid generator. Therefore, the composition can provide all of CDU, MEEF and LWR properties at sufficient levels. Although the reason is not clear, it is presumed that the acid diffusion length and the acidity are optimized as a whole synergistically or additively by using a plurality of certain radiation-sensitive acid generators, and thereby various resist properties are improved.

Preferably, the compound represented by the above formula (1) is a compound represented by the following formula (1'), the compound represented by the above formula (2) is a compound represented by the following formula (2'), and the compound represented by the above formula (3) is a compound represented by the following formula (3'):

[Formula 2]

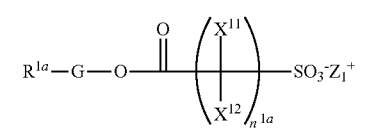

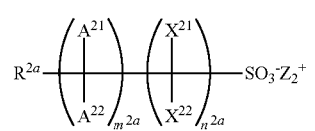

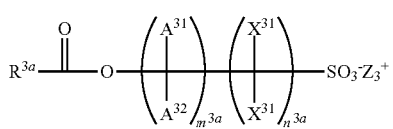

(In the formulae (1') to (3'), $R^{1a}$, $R^{2a}$ and $R^{3a}$ are each independently a substituted or unsubstituted alicyclic group;

$X^{11}$, $X^{12}$, $X^{21}$, $X^{22}$, $X^{31}$ and $X^{32}$ are each independently a fluorine atom, or a monovalent fluorinated chain hydrocarbon group having a carbon number of 1 to 10;

$A^{21}$, $A^{22}$, $A^{31}$ and $A^{32}$ are each independently a hydrogen atom, or a chain hydrocarbon group having a carbon number of 1 to 10;

$m^{2a}$ and $m^{3a}$ are each independently 0 or 1;

$n^{1a}$, $n^{2a}$ and $n^{3a}$ are each independently 1 or 2;

G has the same meaning as in the above formula (1); and $Z_1^+$, $Z_2^+$ and $Z_3^+$ have the same meaning as in the above formulae (1) to (3), respectively.)

The radiation-sensitive resin composition can effectively provide CDU, MEEF and LWR properties at higher level by including at least two of compounds represented by the above formulae (1') to (3') as the radiation-sensitive acid generator.

Preferably, the radiation-sensitive acid generator is:

the compound represented by the above formula (1) and the compound represented by the above formula (2);

the compound represented by the above formula (1) and the compound represented by the above formula (3); or the compound represented by the above formula (1), the compound represented by the above formula (2) and the compound represented by the above formula (3).

The various resist properties can be further improved by including at least one of the compounds (2) and (3) as the radiation-sensitive acid generator in addition to the compound (1).

When at least one of the compounds (2) and (3) is included as the radiation-sensitive acid generator in addition to the compound (1), a content of the compound represented by the above formula (1) is preferably not less than 1 part by mass and not more than 45 parts by mass based on 100 parts by mass of the resin. Thereby, the various resist properties can be improved effectively.

Preferably, each of a molecular weight of an anionic moiety in the radiation-sensitive acid generator is 230 or more. Thereby, it is possible to control the diffusion length of an acid generated from the radiation-sensitive acid generator to the suitable range, and provide various resist properties at higher level.

Preferably, the radiation-sensitive resin composition further includes an acid diffusion controlling agent. Accordingly, it is possible to improve the contrast between an exposed part and a non-exposed part, and thereby further improve various resist properties.

Preferably, the acid diffusion controlling agent is a radiation-sensitive weak acid generator that generates an acid incapable of inducing dissociation of the acid-dissociable group in a condition that an acid generated by the radiation-sensitive acid generator dissociates the acid-dissociable group.

The present invention also relates to a method of forming a resist pattern, including the steps of:

forming a resist film from the radiation-sensitive resin composition;

exposing the resist film; and developing the exposed resist film.

According to the method of forming a resist pattern, a high-quality resist pattern can be formed effectively because of using the radiation-sensitive resin composition having improved various resist properties.

DETAILED DESCRIPTION OF THE PREFERRED EMBODIMENTS

<Radiation-Sensitive Resin Composition>

The radiation-sensitive resin composition according to the present embodiment (hereinafter, also referred simply as a "composition") includes a resin, a radiation-sensitive acid generator, and a solvent. The composition may also include an optional ingredient as long as the effect of the present invention is not impaired.

(Resin)

The resin is an aggregation of polymers, each polymer including a structure unit having an acid-dissociable group (hereinafter, also referred as a "structure unit (I)"). (Hereinafter, the resin is also referred as a "base resin".) The "acid-dissociable group" refers to a substituent group with which a hydrogen atom in a group such as a carboxy group, a phenolic hydroxide group, an alcoholic hydroxide group, and a sulfo group is substituted, and the acid-dissociable group is dissociated by an acid. The radiation-sensitive resin composition provides an improved patternability because of the resin including the structure unit (I).

Preferably, the base resin includes a structure unit (II) in addition to the structure unit (I), the structure unit (II) including at least one selected from the group consisting of a lactone structure, a cyclic carbonate structure and a sultone structure as described below. The base resin may include any other structure unit other than the structure unit (I) and the structure unit (II). Each of the structure units will now be described.

[Structure Unit (I)]

The structure unit (I) is a structure unit having an acid-dissociable group. The structure unit (I) is not particularly limited as long as the unit has an acid-dissociable group. Examples of the structure unit (I) include a structure unit having a tertiary alkyl ester moiety; a structure unit having a structure in which a hydrogen atom in a phenolic hydroxide group is substituted with a tertiary alkyl group; and a structure unit having an acetal bond. In terms of improving the patternability of the radiation-sensitive resin composition, the structure unit (I) is preferably a structure unit represented by the following formula (2) (hereinafter, also referred to a "structure unit (I-1)").

[Formula 3]

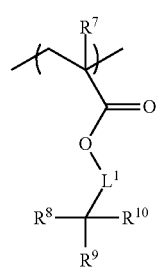

(2)

In the above formula (2), $R^7$ is a hydrogen atom, a fluorine atom, a methyl group, or a trifluoromethyl group; $R^8$ is a hydrogen atom, or a monovalent hydrocarbon group having a carbon number of 1 to 20; $R^9$ and $R^{10}$ are each independently a monovalent chain hydrocarbon group having a carbon number of 1 to 10, or a monovalent alicyclic hydrocarbon group having a carbon number of 3 to 20, or represent a divalent alicyclic group having a carbon number of 3 to 20, which is obtained by combining $R^9$ and $R^{10}$ with the carbon atom to which they are bound; $L^1$ represents a single bond, or a divalent linking group. However, when $L^1$ is the divalent linking group, a carbon atom which is bound to an oxygen atom of —COO— in the above formula (2) is a tertiary carbon, or its structure at the terminal side of the side chain is —COO—.

As $R^7$ described above, in terms of the copolymerizability of monomers resulting in the structure unit (I-1), a hydrogen atom or a methyl group is preferred. A methyl group is more preferred.

Examples of the monovalent hydrocarbon group having a carbon number of 1 to 20 represented by $R^8$ as described above include a chain hydrocarbon group having a carbon number of 1 to 10, a monovalent alicyclic hydrocarbon group having a carbon number of 3 to 20, and a monovalent aromatic hydrocarbon group having a carbon number of 6 to 20.

Examples of the chain hydrocarbon group having a carbon number of 1 to 10 represented by $R^8$ to $R^{10}$ as described above include a straight or branched chain saturated hydrocarbon group having a carbon number of 1 to 10, or a straight or branched chain unsaturated hydrocarbon group having a carbon number of 1 to 10.

Examples of the alicyclic a hydrocarbon group having a carbon number of 3 to 20 represented by $R^8$ to $R^{10}$ as described above include a monocyclic or polycyclic saturated hydrocarbon group, or a monocyclic or polycyclic unsaturated hydrocarbon group. Preferred examples of the monocyclic saturated hydrocarbon group include a cyclopentyl group, a cyclohexyl group, a cycloheptyl group, and a cyclooctyl group. Preferred examples of the polycyclic cycloalkyl group include a bridged alicyclic hydrocarbon group including a norbornyl group, an adamantyl group, a tricyclodecyl group, and a tetracyclododecyl group. The bridged alicyclic hydrocarbon group refers to a polycyclic alicyclic hydrocarbon group in which non-adjacent two carbon atoms of the alicyclic ring are bonded together via a binding chain having one or more carbon atoms.

Examples of the monovalent aromatic hydrocarbon group having a carbon number of 6 to 20 represented by $R^8$ as described above include an aryl group including a phenyl group, a tolyl group, a xylyl group, a naphthyl group, and an anthryl group; and an aralkyl group including a benzyl group, a phenethyl group, and a naphthyl methyl group.

Preferred examples of $R^8$ include a straight or branched chain saturated hydrocarbon group having a carbon number of 1 to 10, and an alicyclic hydrocarbon group having a carbon number of 3 to 20.

The divalent alicyclic group having a carbon number of 3 to 20, which is obtained by combining a combination of the chain hydrocarbon group or the alicyclic hydrocarbon group represented by $R^9$ and $R^{10}$ with the carbon atom to which they are bound, is not particularly limited as long as the group is a group obtained by removing two hydrogen atoms from the same carbon atom of a monocyclic or polycyclic alicyclic hydrocarbon carbocyclic ring having the same number of carbon atoms as described above. The group may be a monocyclic hydrocarbon group or a polycyclic hydrocarbon group. The polycyclic hydrocarbon group may be a bridged alicyclic hydrocarbon group or a fused alicyclic hydrocarbon group, and may be a saturated hydrocarbon group or an unsaturated hydrocarbon group. The fused alicyclic hydrocarbon group refers to a polycyclic alicyclic hydrocarbon group in which a plurality of alicyclic rings shares one side (a bond between adjacent two carbon atoms).

Preferred examples of the saturated hydrocarbon group in the monocyclic alicyclic hydrocarbon group include a cyclopentanediyl group, a cyclohexanediyl group, a cycloheptanediyl group, and a cyclooctanediyl group. Preferred examples of the unsaturated hydrocarbon group include a cyclopentenediyl group, a cyclohexenediyl group, a cycloheptenediyl group, a cyclooctenediyl group, and a cyclodecenediyl group. Preferred examples of the polycyclic alicyclic hydrocarbon group include a bridged alicyclic saturated hydrocarbon group. For example, a group such as a bicyclo[2.2.1]heptan-2,2-diyl group (a norbornane-2,2-diyl group), a bicyclo[2.2.2]octan-2,2-diyl group, or a tricyclo[3.3.1.1$^{3,7}$]decan-2,2-diyl group (an adamantane-2,2-diyl group) is preferred.

Examples of the divalent linking group represented by $L^1$ as described above include an alkanediyl group, a cycloalkanediyl group, an alkenediyl group, *—$R^{LA}$O—, and —$R^{LB}$COO—. (* refers to a bond to the side of oxygen.) However, when the group is other than —$R^{LB}$COO—, the carbon atom connecting to the oxygen atom of —COO— in the above formula (2) is a tertiary carbon, and the carbon atom does not have any hydrogen atom. The tertiary carbon is obtained when there are two bonds from the same carbon atom in the group, or when one or two substituent groups are further connected to the carbon atom having one of the bonds in the group. A part of or all of hydrogen atoms in the group may be substituted with a halogen atom including a fluorine atom or chlorine atom, or a cyano group.

The alkanediyl group is preferably an alkanediyl group having a carbon number of 1 to 8.

Examples of the cycloalkanediyl group include a monocyclic cycloalkanediyl group including a cyclopentanediyl group and a cyclohexanediyl group; and a polycyclic cycloalkanediyl group including a norbornanediyl group and an adamantanediyl group. The cycloalkanediyl group is preferably a cycloalkanediyl group having a carbon number of 5 to 12.

Examples of the alkenediyl group include an ethenediyl group, a propenediyl group, and a butenediyl group. The alkenediyl group is preferably an alkenediyl group having a carbon number of 2 to 6.

Examples of $R^{LA}$ in the *—$R^{LA}$O— include the alkanediyl group, the cycloalkanediyl group, and the alkenediyl group as each described above. Examples of $R^{LB}$ in *—$R^{LB}$COO— include the alkanediyl group, the cycloalkanediyl group, and the alkenediyl group as each described above, and an arenediyl group. Examples of the arenediyl group include a phenylene group, a tolylene group, and a naphthylene group. The arenediyl group is preferably an arenediyl group having a carbon number of 6 to 15.

Among them, preferably, $R^8$ is an alkyl group having a carbon number of 1 to 4, and $R^9$ and $R^{10}$ are a monocyclic or polycyclic cycloalkane structure in which the alicyclic structure is obtained by combining $R^9$ and $R^{10}$ with the carbon atom to which they are bound. Preferably, L is a single bond or *—$R^{LA}$O—. Preferred $R^{LA}$ is an alkanediyl group.

Examples of the structure unit (I-1) include structure units represented by the following formulae (3-1) to (3-4) (hereinafter, also referred as "structure unit (I-1-1) to (I-1-4)").

[Formula 4]

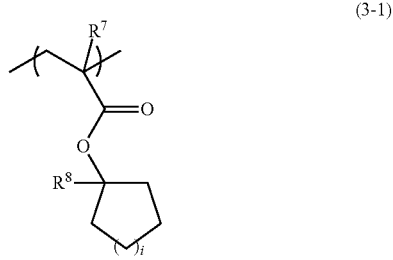

(3-1)

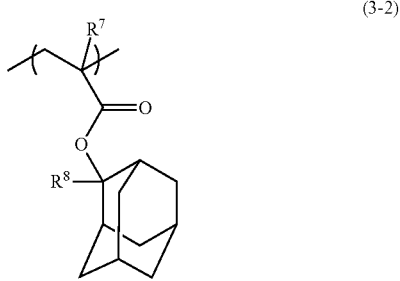

(3-2)

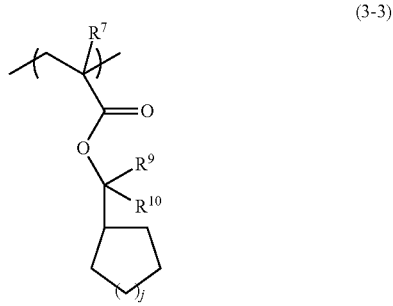

(3-3)

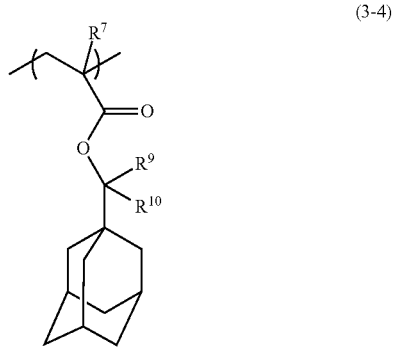

(3-4)

In the above formulae (3-1) to (3-4), $R^7$ to $R^{10}$ have the same meaning as in the above formula (2); and i and j are each independently an integer of 1 to 4. $n_A$ is 0 or 1.

i and j are preferably 1. $R^8$ to $R^{10}$ are preferably a methyl group, an ethyl group, or an iso-propyl group.

Among them, the structure unit (I-1) is preferably the structure unit (I-1-1) or the structure unit (I-1-2), more preferably a structure unit having a cyclopentane structure or a structure unit having an adamantane structure, further preferably a structure unit derived from 1-alkylcyclopentyl (meth)acrylate, a structure unit derived from 2-alkyladamantyl (meth)acrylate, and particularly preferably a structure unit derived from 1-methylcyclohexyl (meth)acrylate or a structure unit derived from 2-ethyladamantyl (meth)acrylate.

The base resin may include one type of the structure unit (I), or two or more types of the structure units (I) in combination.

The lower limit of the content by percent of the structure unit (I) is preferably 10 mol %, more preferably 15 mol %, further preferably 20 mol %, and more further preferably 30 mol % based on the total structure units as the component of the base resin. The upper limit of the content by percent is preferably 90 mol %, more preferably 80 mol %, further preferably 75 mol %, and particularly preferably 70 mol %. By adjusting the content by percent of the structure unit (I) within the ranges, the patternability of the radiation-sensitive resin composition can be further improved.

[Structure Unit (II)]

The structure unit (II) is a structure unit including at least one selected from the group consisting of a lactone structure, a cyclic carbonate structure and a sultone structure. The solubility of the base resin into a developer can be adjusted by further introducing the structure unit (II). As a result, the radiation-sensitive resin composition can provide improved lithography properties such as the resolution. The adhesion between a resist pattern formed from the base resin and a substrate can also be improved.

Examples of the structure unit (II) include structure units represented by the following formulae (T-1) to (T-10)

[Formula 5]

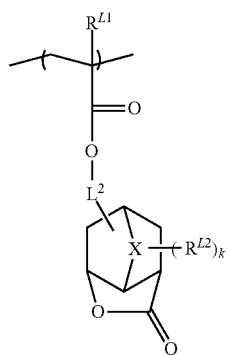
(T-1)

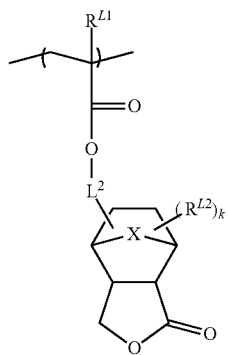
(T-2)

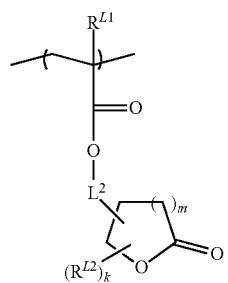
(T-3)

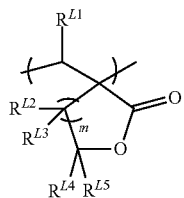
(T-4)

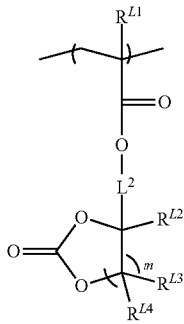
(T-5)

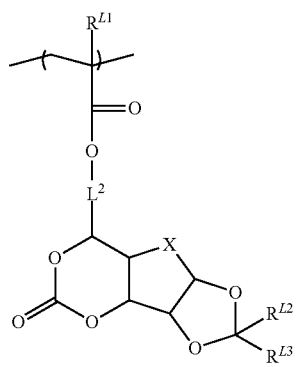
(T-6)

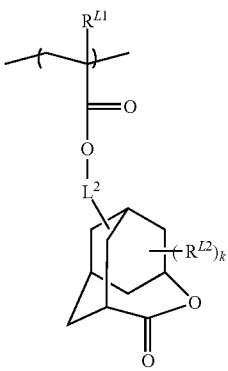
(T-7)

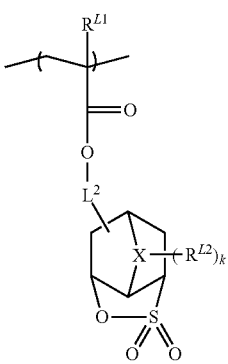
(T-8)

-continued

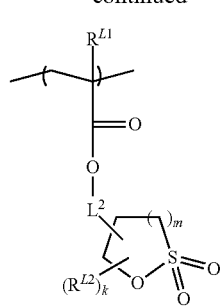

(T-9)

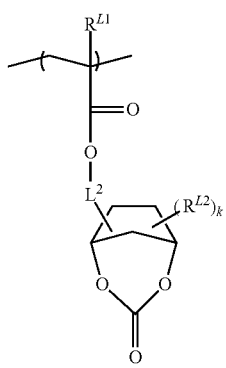

(T-10)

In the above formulae, $R^{L1}$ is a hydrogen atom, a fluorine atom, a methyl group, or a trifluoromethyl group; $R^{L2}$ to $R^{L5}$ are each independently a hydrogen atom, an alkyl group having a carbon number of 1 to 4, a cyano group, a trifluoromethyl group, a methoxy group, a methoxycarbonyl group, a hydroxy group, a hydroxymethyl group, or a dimethylamino group; $R^{L4}$ and $R^{L5}$ may be a divalent alicyclic group having a carbon number of 3 to 8, which is obtained by combining $R^{L4}$ and $R^{L5}$ with the carbon atom to which they are bound. $L^2$ is a single bond, or a divalent linking group; X is an oxygen atom or a methylene group; k is an integer of 0 to 3; and m is an integer of 1 to 3.

Example of the divalent alicyclic group having a carbon number of 3 to 8, which is composed of a combination of $R^{L4}$ and $R^{L5}$ with the carbon atom to which they are bound, includes the divalent alicyclic group having a carbon number of 3 to 8 in the divalent alicyclic group having a carbon number of 3 to 20, which is composed of a combination of the chain hydrocarbon group or the alicyclic hydrocarbon group represented by $R^9$ and $R^{10}$ in the above formula (2) with the carbon atom to which they are bound. One or more hydrogen atoms on the alicyclic group may be substituted with a hydroxy group.

Examples of the divalent linking group represented by $L^2$ as described above include a divalent straight or branched chain hydrocarbon group having a carbon number of 1 to 10; a divalent alicyclic hydrocarbon group having a carbon number of 4 to 12; and a group composed of one or more of the hydrocarbon group thereof and at least one group of —CO—, —O—, —NH— and —S—.

Among them, the structure unit (II) is preferably a group having a lactone structure, more preferably a group having a norbornane lactone structure, and further preferably a group derived from a norbornane lactone-yl (meth)acrylate.

The lower limit of the content by percent of the structure unit (II) is preferably 20 mol %, more preferably 25 mol %, and further preferably 30 mol % based on the total structure units as the component of the base resin. The upper limit of the content by percent is preferably 80 mol %, more preferably 70 mol %, and further preferably 60 mol %. By adjusting the content by percent of the structure unit (II) within the ranges, the radiation-sensitive resin composition can provide improved lithography properties such as the resolution.

The adhesion between the formed resist pattern and the substrate can also be improved.

[Other Structure Unit]

The base resin may also include any other structure unit in addition to the structure units (I) and (II). Example of the other structure unit includes a structure unit having a polar group, provided that the structure unit within the scope of the structure unit (II) is excluded. The base resin can adjust its solubility into the developer by further including the structure unit having a polar group in the resin. As a result, the radiation-sensitive resin composition can provide improved lithography properties such as the resolution. Examples of the polar group include a hydroxy group, a carboxy group, a cyano group, a nitro group, and a sulfonamide group. Among them, a hydroxy group or a carboxy group is preferred, and a hydroxy group is more preferred.

Example of the structure unit having a polar group includes structure units represented by the following formulae.

[Formula 6]

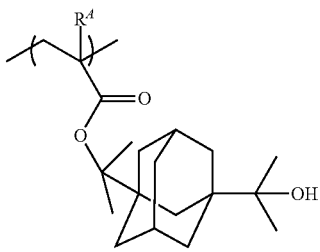

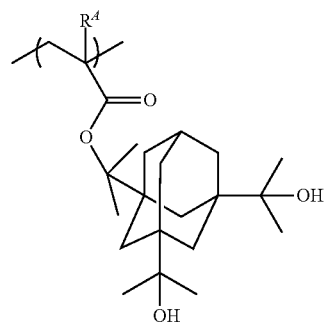

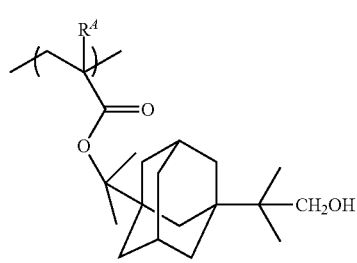

-continued

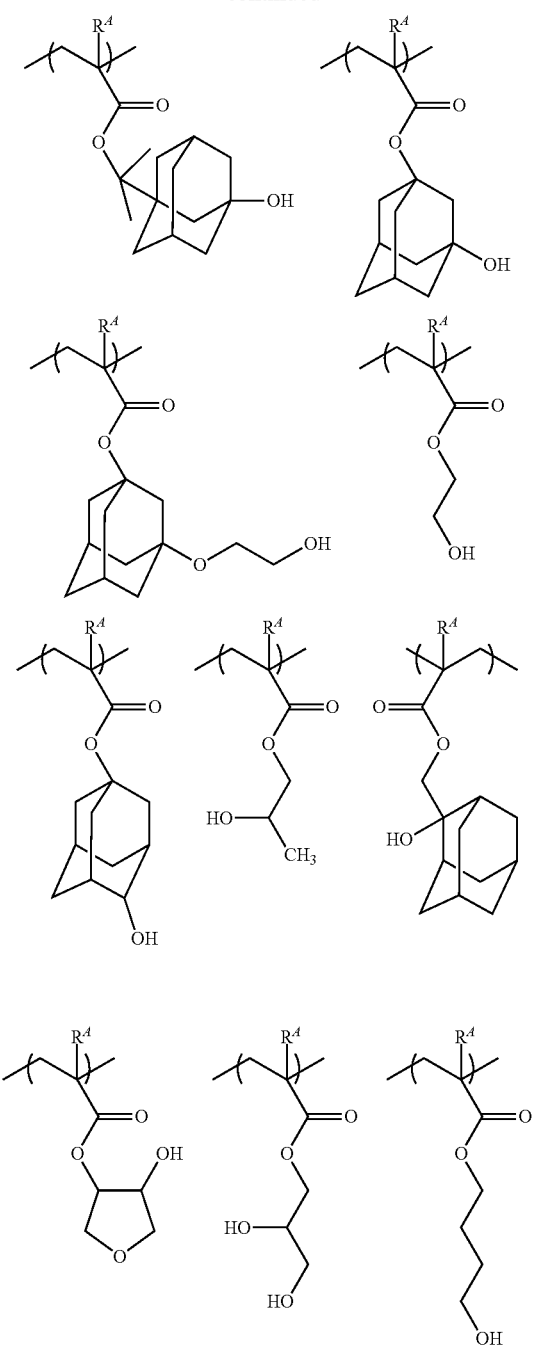

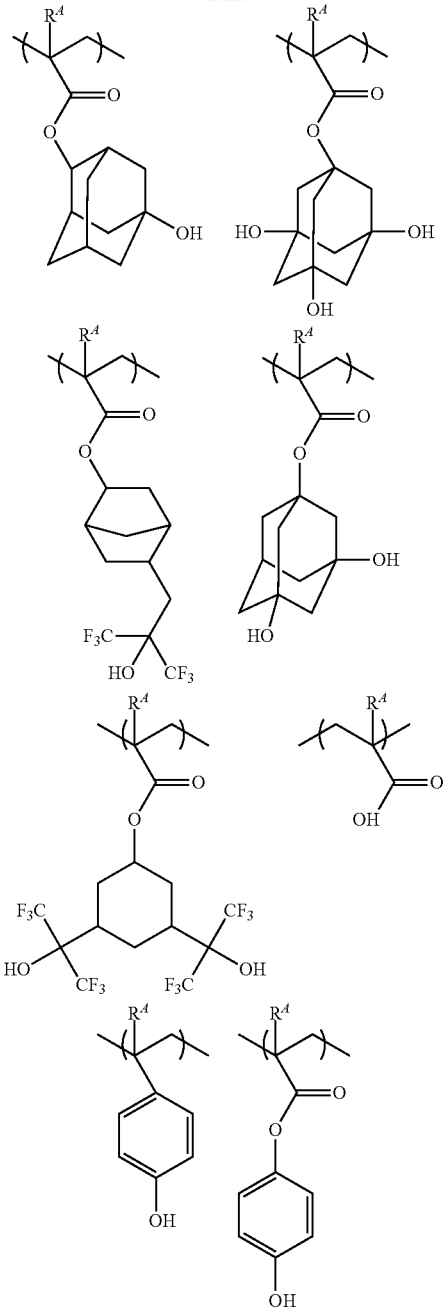

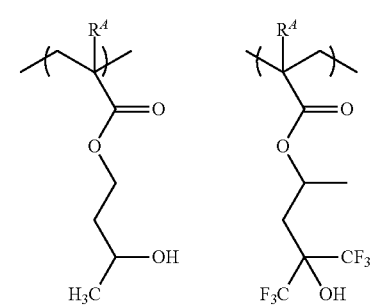

In the above formulae, $R^A$ is a hydrogen atom, a fluorine atom, a methyl group, or a trifluoromethyl group.

When the base resin includes the structure unit having a polar group, the lower limit of the content by percent of the structure unit having a polar group is preferably 5 mol %, more preferably 10 mol %, and further preferably 20 mol % based on the total structure units as the component of the base resin. The upper limit of the content by percent is preferably 90 mol %, more preferably 80 mol %, and further preferably 70 mol %. By adjusting the content by percent of the structure unit having a polar group within the ranges, the radiation-sensitive resin composition can provide improved lithography properties such as the resolution.

The base resin may also include a structure unit derived from a hydroxystyrene (hereinafter, also referred as a "structure unit (III)") as the other structure unit in addition to the structure unit having a polar group. The structure unit (III) contributes to the improvement of the etching resistance and the improvement of the difference in solubility into the developer between the exposed part and the non-exposed part (solubility contrast). In particular, the resin can be suitably applied for a pattern formation by exposing to radiation having a wavelength of 50 nm or less, for example, an electron beam or EUV. In this case, the resin has preferably the structure unit (I) and the structure unit (III).

However, the polymerization of the hydroxystyrene is inhibited by the effect of its phenolic hydroxide group. Therefore, hydroxystyrene is polymerized in a state that the phenolic hydroxide group is preferably protected with a protecting group such as an alkali-dissociable group, and then hydrolyzed for the deprotection of the phenolic hydroxide group to obtain the structure unit (III). The structure unit from which the structure unit (III) is obtained by the hydrolysis is preferably represented by the following formula (4).

[Formula 7]

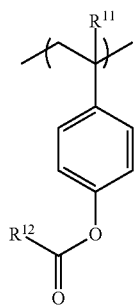

(4)

In the above formula (4), $R^{11}$ is a hydrogen atom, a fluorine atom, a methyl group, or a trifluoromethyl group; $R^{12}$ is a monovalent hydrocarbon group having a carbon number of 1 to 20, or an alkoxy group. Example of the monovalent hydrocarbon group having a carbon number of 1 to 20 of $R^{12}$ includes the monovalent hydrocarbon group having a carbon number of 1 to 20 of $R^8$ in the structure unit (I). Examples of the alkoxy group include a methoxy group, an ethoxy group and a tert-butoxy group.

Preferred $R^{12}$ is an alkyl group and an alkoxy group. A methyl group or a tert-butoxy group is more preferred.

When the resin is for exposing to radiation having a wavelength of 50 nm or less, the lower limit of the content by percent of the structure unit (III) is preferably 20 mol %, and more preferably 30 mol % based on the total structure units as the component of the resin. The upper limit of the content by percent is preferably 80 mol %, and more preferably 70 mol %.

(Synthesis Method of Base Resin)

For example, the base resin can be synthesized by polymerizing each monomer for providing each structure unit with a radical polymerization initiator or the like in a suitable solvent.

Examples of the radical polymerization initiator include an azo-based radical initiator, including azobisisobutyronitrile (AIBN), 2,2'-azobis(4-methoxy-2,4-dimethylvaleronitrile), 2,2'-azobis(2-cyclopropylpropanenitrile), 2,2'-azobis (2,4-dimethylvaleronitrile), and dimethyl 2,2'-azobisisobutyrate; and peroxide-based radical initiator, including benzoyl peroxide, t-butyl hydroperoxide, and cumene hydroperoxide. Among them, AIBN or dimethyl 2,2'-azobisisobutyrate is preferred, and AIBN is more preferred. The radical initiator may be used alone, or two or more radical initiators may be used in combination.

Examples of the solvent used for the polymerization include alkanes including n-pentane, n-hexane, n-heptane, n-octane, n-nonane, and n-decane;

cycloalkanes including cyclohexane, cycloheptane, cyclooctane, decalin, and norbornane;

aromatic hydrocarbons including benzene, toluene, xylene, ethylbenzene, and cumene;

halogenated hydrocarbons including chlorobutanes, bromohexanes, dichloroethanes, hexamethylenedibromide, and chlorobenzenes;

saturated carboxylate esters, including ethyl acetate, n-butyl acetate, i-butyl acetate, and methyl propionate;

ketones including acetone, methyl ethylketone, 4-methyl-2-pentanone, and 2-heptanone;

ethers including tetrahydrofuran, dimethoxyethanes, and diethoxyethanes; and alcohols including methanol, ethanol, 1-propanol, 2-propanol, and 4-methyl-2-pentanol. The solvent used for the polymerization may be used alone, or two or more solvents may be used in combination.

The reaction temperature of the polymerization is typically from 40° C. to 150° C., and preferably from 50° C. to 120° C. The reaction time is typically from 1 hour to 48 hours, and preferably from 1 hour to 24 hours.

Although the molecular weight of the base resin is not particularly limited, the weight average molecular weight (Mw) is preferably not less than 1,000 and not more than 50,000, more preferably not less than 2,000 and not more than 30,000, further preferably not less than 3,000 and not more than 15,000, and particularly preferably not less than 4,000 and not more than 12,000, as determined by Gel Permeation Chromatography (GPC) relative to standard polystyrene. If the Mw of the base resin is below the lower limits, the thermal resistance of the resulting resist film may be decreased. If the Mw of the base resin is beyond the upper limits, the developability of the resist film may be decreased.

For the base resin, the ratio of Mw to the number average molecular weight (Mn) as determined by GPC relative to standard polystyrene (Mw/Mn) is typically not less than 1 and not more than 5, preferably not less than 1 and not more than 3, and more preferably not less than 1 and not more than 2.

The Mw and Mn of the resin according to the present invention are amounts measured by using Gel Permeation Chromatography (GPC) with the condition as described below.

GPC column: two G2000HXL, one G3000HXL, and one G4000HXL (all manufactured from Tosoh Corporation)

Column temperature: 40° C.

Eluting solvent: tetrahydrofuran

Flow rate: 1.0 mL/min

Sample concentration: 1.0% by mass

Sample injection amount: 100 μL

Detector: Differential Refractometer

Reference material: monodisperse polystyrene

The content of the base resin is preferably not less than 70% by mass, more preferably not less than 80% by mass, and further preferably not less than 85% by mass based on the total solid content of the radiation-sensitive resin composition.

(Other Resin)

The radiation-sensitive resin composition of this embodiment may include a resin having higher content by mass of fluorine atoms than the base resin as described above (hereinafter, also referred as a "high fluorine-containing resin") as the other resin. When the radiation-sensitive resin composition includes the high fluorine-containing resin, the high fluorine-containing resin can be localized on the surface layer of the resist film compared to the base resin. Therefore, the water repellency of the surface of the resist film can be improved during the immersion exposure.

The high fluorine-containing resin is preferably one having a structure unit represented by the following formula (5) (hereinafter, also referred as a "structure unit (IV)") in addition to the structure unit (I) in the base resin as described above.

[Formula 8]

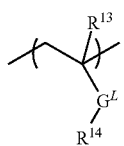

(5)

In the above formula (5), $R^{13}$ is a hydrogen atom, a methyl group, or a trifluoromethyl group; G is a single bond, an oxygen atom, a sulfur atom, —COO—, —SO$_2$ONH—, —CONH—, or —OCONH—; $R^{14}$ is a monovalent fluorinated chain hydrocarbon group having a carbon number of 1 to 20, or a monovalent fluorinated alicyclic hydrocarbon group having a carbon number of 3 to 20.

As $R^{13}$ as described above, in terms of the copolymerizability of monomers resulting in the structure unit (IV), a hydrogen atom or a methyl group is preferred, and a methyl group is more preferred.

As $G^L$ as described above, in terms of the copolymerizabilityof monomers resulting in the structure unit (IV), a single bond or —COO— is preferred, and —COO— is more preferred.

Example of the monovalent fluorinated chain hydrocarbon group having a carbon number of 1 to 20 represented by $R^{14}$ as described above includes a group in which a part of or all of hydrogen atoms in the straight or branched chain alkyl group having a carbon number of 1 to 20 is/are substituted with a fluorine atom.

Example of the monovalent fluorinated alicyclic hydrocarbon group having a carbon number of 3 to 20 represented by $R^{14}$ as described above includes a group in which a part of or all of hydrogen atoms in the monocyclic or polycyclic hydrocarbon group having a carbon number of 3 to 20 is/are substituted with a fluorine atom.

The $R^{14}$ as described above is preferably a fluorinated chain hydrocarbon group, more preferably a fluorinated alkyl group, and further preferably 2,2,2-trifluoroethyl group, 1,1,1,3,3,3-hexafluoropropyl group and 5,5,5-trifluoro-1,1-diethylpentyl group.

When the high fluorine-containing resin has the structure unit (IV), the lower limit of the content by percent of the structure unit (IV) is preferably 10 mol %, more preferably 15 mol %, further preferably 20 mol %, and particularly preferably 25 mol % based on the total structure units as the component of the high fluorine-containing resin. The upper limit of the content by percent is preferably 60 mol %, more preferably 50 mol %, and further preferably 40 mol %. By adjusting the content by percent of the structure unit (IV) within the ranges, the content by mass percent of fluorine atoms of the high fluorine-containing resin can be suitably adjusted to promote the localization of the high fluorine-containing resin on the surface layer of the resist film. Therefore, the water repellency of the surface of the resist film can be improved during the immersion exposure.

The high fluorine-containing resin may include a structure unit having a fluorine atom represented by the following formula (f-2) (hereinafter, also referred as a "structure unit (V)") in addition to the structure unit (IV). The solubility of the high fluorine-containing resin into an alkaline developing solution can be improved by including the structure unit (f-2), and thereby prevent from generating the development defect.

[Formula 9]

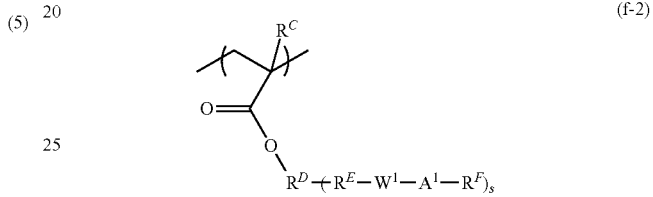

(f-2)

The structure unit (V) is classified into two groups: a unit having an alkali soluble group (x); and a unit having a group (y) in which the solubility into the alkaline developing solution is increased by the dissociation by alkali (hereinafter, simply referred as an "alkali-dissociable group"). In both cases of (x) and (y), $R^C$ in the above formula (f-2) is a hydrogen atom, a fluorine atom, a methyl group, or a trifluoromethyl group; $R^D$ is a single bond, a hydrocarbon group having a carbon number of 1 to 20 with the valency of (s+1), a structure in which an oxygen atom, a sulfur atom, —NR$^{dd}$—, a carbonyl group, —COO— or —CONH— is connected to the terminal on $R^E$ side of the hydrocarbon group, or a structure in which a part of hydrogen atoms in the hydrocarbon group is substituted with an organic group having a hetero atom; $R^{dd}$ is a hydrogen atom, or a monovalent hydrocarbon group having a carbon number of 1 to 10; and s is an integer of 1 to 3.

When the structure unit (V) has the alkali soluble group (x), $R^F$ is a hydrogen atom; $A^1$ is an oxygen atom, —COO—* or —SO$_2$O—*; * refers to a bond to $R^F$; $W^1$ is a single bond, a hydrocarbon group having a carbon number of 1 to 20, or a divalent fluorinated hydrocarbon group. When $A^1$ is an oxygen atom, $W^1$ is a fluorinated hydrocarbon group having a fluorine atom or a fluoroalkyl group on the carbon atom connecting to $A^1$. $R^E$ is a single bond, or a divalent organic group having a carbon number of 1 to 20. When s is 2 or 3, a plurality of $R^E$, $W^1$, $A^1$ and $R^F$ may be each identical or different. The affinity of the high fluorine-containing resin into the alkaline developing solution can be improved by including the structure unit (V) having the alkali soluble group (x), and thereby prevent from generating the development defect. As the structure unit (V) having the alkali soluble group (x), particularly preferred is a structure unit in which $A^1$ is an oxygen atom and $W^1$ is a 1,1,1,3,3,3-hexafluoro-2,2-methanediyl group.

When the structure unit (V) has the alkali-dissociable group (y), $R^F$ is a monovalent organic group having carbon number of 1 to 30; $A^1$ is an oxygen atom, —NR$^{aa}$—, —COO—*, or —SO$_2$O—*; $R^{aa}$ is a hydrogen atom, or a monovalent hydrocarbon group having a carbon number of 1 to 10; * refers to a bond to $R^F$; $W^1$ is a single bond, or a divalent fluorinated hydrocarbon group having a carbon number of 1 to 20; $R^E$ is a single bond, or a divalent organic group having a carbon number of 1 to 20. When $A^1$ is —COO—* or —SO$_2$O—*, $W^1$ or $R^F$ has a fluorine atom on the carbon atom connecting to $A^1$ or on the carbon atom adjacent to the carbon atom. When $A^1$ is an oxygen atom, $W^1$ and $R^E$ are a single bond; $R^D$ is a structure in which a carbonyl group is connected at the terminal on $R^E$ side of the hydrocarbon group having a carbon number of 1 to 20; and $R^F$ is an organic group having a fluorine atom. When s is 2 or 3, a plurality of $R^E$, $W^1$, $A^1$ and $R^F$ may be each identical or different. The surface of the resist film is changed from hydrophobic to hydrophilic in the alkaline developing step by including the structure unit (V) having the alkali-dissociable group (y). As a result, the affinity of the high fluorine-containing resin into the alkaline developing solution can be significantly improved, and thereby prevent from generating the development defect more efficiently. As the structure unit (V) having the alkali-dissociable group (y), particularly preferred is a structure unit in which $A^1$ is —COO—*, and $R^F$ or $W^1$, or both is/are a fluorine atom.

In terms of the copolymerizability of monomers resulting in the structure unit (V), $R^C$ is preferably a hydrogen atom or a methyl group, and more preferably a methyl group.

When $R^E$ is a divalent organic group, $R^E$ is preferably a group having a lactone structure, more preferably a group having a polycyclic lactone structure, and further preferably a group having a norbornane lactone structure.

When the high fluorine-containing resin has the structure unit (V), the lower limit of the content by percent of the structure unit (V) is preferably 10 mol %, more preferably 20 mol %, further preferably 30 mol %, and particularly preferably 35 mol % based on the total structure units as the component of the high fluorine-containing resin. The upper limit of the content by percent is preferably 90 mol %, more preferably 75 mol %, and further preferably 60 mol %. By adjusting the content by percent of the structure unit (V) within the ranges, the water repellency of the surface of the resist film can be further improved during the immersion exposure.

The lower limit of Mw of the high fluorine-containing resin is preferably 1,000, more preferably 2,000, further preferably 3,000, and particularly preferably 5,000. The upper limit of Mw is preferably 50,000, more preferably 30,000, further preferably 20,000, and particularly preferably 15,000.

The lower limit of the Mw/Mn of the high fluorine-containing resin is typically 1, and more preferably 1.1. The upper limit of the Mw/Mn is typically 5, preferably 3, more preferably 2, and further preferably 1.7.

The lower limit of the content of the high fluorine-containing resin is preferably 0.1% by mass, more preferably 0.5% by mass, further preferably 1% by mass, and even further preferably 1.5% by mass based on the total solid content of the radiation-sensitive resin composition. The upper limit of the content is preferably 20% by mass, more preferably 15% by mass, further preferably 10% by mass, and particularly preferably 7% by mass.

The lower limit of the content of the high fluorine-containing resin is preferably 0.1 part by mass, more preferably 0.5 part by mass, further preferably 1 part by mass, and particularly preferably 1.5 part by mass based on 100 parts by mass of total base resins. The upper limit of the content is preferably 15 parts by mass, more preferably 10 parts by mass, further preferably 8 parts by mass, and particularly preferably 5 parts by mass.

By adjusting the content of the high fluorine-containing resin within the ranges, the high fluorine-containing resin can be localized on the surface layer of the resist film more efficiently. Therefore, the water repellency of the surface of the resist film can be improved during the immersion exposure. The radiation-sensitive resin composition may contain one type of the high fluorine-containing resin, or two or more high fluorine-containing resins in combination.

(Method for Synthesizing High Fluorine-Containing Resin)

The high fluorine-containing resin can be synthesized by the similar method for the base resin as described above.

(Radiation-Sensitive Acid Generator)

The radiation-sensitive acid generator includes at least two of compounds represented by the following formulae (1) to (3), provided that the compound represented by the formula (1) and the compound represented by the formula (3) within the scope of the compound represented by the formula (2) are excluded.

[Formula 10]

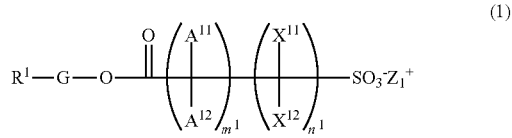

(1)

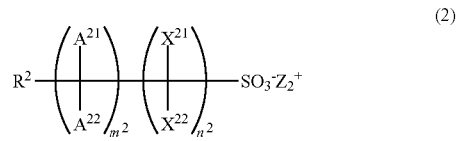

(2)

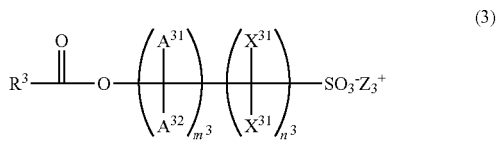

(3)

In the formulae (1) to (3), $R^1$, $R^2$ and $R^3$ are each independently a group having a cyclic structure;

$X^{11}$, $X^{12}$, $X^{21}$, $X^{22}$, $X^{33}$ and $X^{32}$ are each independently a hydrogen atom, a fluorine atom, or a fluorinated hydrocarbon group, provided that both $X^{11}$ and $X^{12}$, both $X^{21}$ and $X^{22}$, and both $X^{31}$ and $X^{32}$ are not a hydrogen atom, respectively;

$A^{11}$, $A^{12}$, $A^{21}$, $A^{22}$, $A^{31}$ and $A^{32}$ are each independently a hydrogen atom, or a hydrocarbon group having a carbon number of 1 to 20;

$m^1$, $m^2$ and $m^3$ are each independently an integer of 0 to 5;

$n^1$, $n^2$ and $n^3$ are each independently an integer of 1 to 4;

G is a single bond, or a divalent linking group; and $Z_1^+$, $Z_2^+$ and $Z_3^+$ are each independently a monovalent onium cation.

The group having a cyclic structure is not particularly limited as long as the group has a cyclic structure. The cyclic structure may be an alicyclic structure, an aromatic ring structure, or a heterocyclic ring structure, and a monocyclic or polycyclic structure, and saturated or unsaturated. The cyclic structure may be formed only by a ring structure, or may have a chain structure in part thereof. When the cyclic structure has a chain structure in part thereof, a hetero atom such as O or S may be included between a carbon-carbon bond in the chain structure. The heterocyclic ring structure is not particularly limited. Examples of the heterocyclic ring structure include a lactone structure, a cyclic carbonate structure, a cyclic acetal structure, a cyclic ether structure, a sultone structure, and a cyclic amine structure. The group having a cyclic structure may have a combination of these cyclic structures. Among them, the preferred cyclic structure is an alicyclic group as the alicyclic structure, including a heterocyclic ring structure in which a carbon atom forimng the alicyclic group is substituted with a hetero atom.

The alicyclic group is preferably a group having a alicyclic hydrocarbon group having a carbon number of 3 to 20. Such an alicyclic hydrocarbon group may be monocyclic or polycyclic. Preferred examples of the alicyclic hydrocarbon group include a monocyclic cycloalkyl group, including a cyclopentyl group, a cyclohexyl group, and a cyclooctyl group; and a polycyclic cycloalkyl group, including a norbornyl group, a norbornen-yl group, a tricyclodecanyl group (for example, a tricyclo[5.2.1.0(2,6)]decanyl group), a tetracyclodecanyl group, a tetracyclododecanyl group, and an adamantyl group. The carbon forimng the alicyclic group (i.e., a carbon contributing to the formation of the ring) may be a carbonyl carbon. The carbon forimng the alicyclic group may also be substituted with a hetero atom.

When a part of the carbon forimng the alicyclic group is a carbonyl carbon, the specific examples of the group include an oxocycloalkyl group having a carbon number of 6 to 10, including a 2-oxo-cyclopentyl group, a 2-oxo-cyclohexyl group, a 2-oxo-cycloheptyl group, a 2-oxo-methyl cyclohexyl group, a 2-oxo-norbornyl group, a 2-oxo-bornyl group, and a 6-oxo-1-adamantyl group.

Examples of the heterocyclic ring structure in which the carbon forimng the alicyclic group is substituted with a hetero atom include cyclic structures located at the terminal side with respect to $L^2$ in the above formulae (T-1) to (T-3), and (T-5) to (T-10); and structures having a cyclic acetal represented by the following formulae (S-1) to (S-2).

[Formula 11]

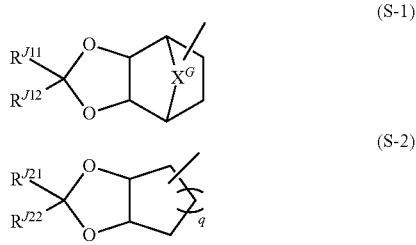

(S-1)

(S-2)

In the above formulae, $R^{J11}$, $R^{J12}$, $R^{J21}$ and $R^{J22}$ are each independently a alicyclic hydrocarbon group having a carbon number of 3 to 20, or an aromatic a hydrocarbon group having a carbon number of 6 to 12; or $R^{J11}$ and $R^{J12}$ are combined together to form a cyclic structure having a carbon number of 4 to 20, or $R^{J21}$ and $R^{J22}$ are combined together to form a cyclic structure having a carbon number of 4 to 20; q is an integer of 1 to 4; $X^G$ is an oxygen atom or a methylene group. Example of the alicyclic hydrocarbon group having a carbon number of 3 to 20 includes the alicyclic hydrocarbon group represented by $R^1$ as described above. Examples of the aromatic hydrocarbon group having a carbon number of 6 to 12 include a phenyl group and a naphthyl group.

Examples of the cyclic structure having a carbon number of 4 to 20, which is obtained by combining $R^{J11}$ and $R^{J12}$, and the cyclic structure having a carbon number of 4 to 20, which is obtained by combining $R^{J21}$ and $R^{J22}$ include a monocyclic cycloalkane structure, including a cyclobutane structure, a cyclopentane structure, and a cyclohexane structure; and a polycyclic cycloalkane structure, including a norbornane structure, an adamantane structure, a tricyclodecane structure, and a tetracyclododecane structure; and a fluorene structure.

Examples of the substituent group with which a hydrogen atom in the alicyclic group may be substituted include a halogen atom, including a fluorine atom, chlorine atom, bromine atom, and iodine atom; a hydroxy group; a carboxy group; a cyano group; a nitro group; a straight or branched chain alkyl group having a carbon number of 1 to 8; a monocyclic or polycyclic cycloalkyl group having a carbon number of 3 to 20; an aryl group, including a phenyl group, a 1-naphthyl group, and a 1-anthracenyl group; an alkoxy group, including a methoxy group, an ethoxy group, and a tert-butoxy group; an alkoxycarbonyl group, including a methoxycarbonyl group, a butoxycarbonyl group, and an adamantylmethyloxycarbonyl group; an alkoxycarbonyloxy group, including a methoxycarbonyloxy group, a butoxycarbonyloxy group, and an adamantylmethyloxycarbonyloxy group; an acyl group, including an acetyl group, a propionyl group, a benzoyl group, and an acryloyl group; and an acyloxy group, including an acetyloxy group, a propionyloxy group, a benzoyloxy group, and an acryloyloxy group.

Examples of the fluorinated hydrocarbon group represented by $X^{11}$, $X^{12}$, $X^{21}$, $X^{22}$, $X^{31}$ and $X^{32}$ include a monovalent fluorinated chain hydrocarbon group having a carbon number of 1 to 20; and a monovalent fluorinated alicyclic hydrocarbon group having a carbon number of 3 to 20.

Examples of the monovalent fluorinated chain hydrocarbon group having a carbon number of 1 to 20 include:
a fluorinated alkyl group, including a trifluoromethyl group, a 2,2,2-trifluoroethyl group, a pentafluoroethyl group, a 2,2,3,3,3-pentafluoropropyl group, a 1,1,1,3,3,3-hexafluoropropyl group, a heptafluoro n-propyl group, a heptafluoro i-propyl group, a nonafluoro n-butyl group, a nonafluoro i-butyl group, a nonafluoro t-butyl group, a 2,2,3,3,4,4,5,5-octafluoro n-pentyl group, a tridecafluoro n-hexyl group, and a 5,5,5-trifluoro-1,1-diethylpentyl group;
a fluorinated alkenyl group, including a trifluoroethenyl group and a pentafluoropropenyl group; and a fluorinated alkynyl group, including a fluoroethynylgroup and a trifluoropropynyl group.

Examples of the monovalent fluorinated alicyclic hydrocarbon group having a carbon number of 3 to 20 include:
a fluorinated cycloalkyl group, including a fluorocyclopentyl group, a difluorocyclopentyl group, a nonafluorocyclopentyl group, a fluorocyclohexyl group, a difluorocyclohexyl group, an undecafluorocyclohexylmethyl group, a fluoronorbornyl group, a fluoroadamantyl group, a fluorobornyl group, a fluoroisobornyl group, a fluorotricyclodecyl group, and a fluorotetracyclodecyl group; and
a fluorinated cycloalkenyl group, including a fluorocyclopentenyl group and a nonafluorocyclohexenyl group.

The fluorinated hydrocarbon group is preferably the monovalent fluorinated chain hydrocarbon group having a carbon number of 1 to 20 as described above, and more preferably a monovalent fluorinated chain hydrocarbon group having a carbon number of 1 to 10. As the monovalent fluorinated chain hydrocarbon group having a carbon number of 1 to 10, a group having a carbon number of 1 to 10 in the monovalent fluorinated chain hydrocarbon group having a carbon number of 1 to 20 as described above can be suitably applied.

Examples of the hydrocarbon group having a carbon number of 1 to 20 represented by $A^{11}$, $A^{12}$, $A^{21}$, $A^{22}$, $A^{31}$ and $A^{32}$ include a chain hydrocarbon group having a carbon number of 1 to 10, a monovalent alicyclic hydrocarbon group having a carbon number of 3 to 20, and a monovalent aromatic hydrocarbon group having a carbon number of 6 to 20.

Examples of the chain hydrocarbon group having a carbon number of 1 to 10 include:
an alkyl group, including a methyl group, an ethyl group, a n-propyl group, an i-propyl group, a n-butyl group, a 2-methylpropyl group, a 1-methylpropyl group, and a t-butyl group;
an alkenyl group, including an ethenyl group, a propenyl group, and a butenyl group; and
an alkynyl group, including an ethynyl group, a propynyl group, and a butynyl group.

Examples of the alicyclic hydrocarbon group having a carbon number of 3 to 20 include:
a monocyclic cycloalkyl group, including a cyclopropyl group, a cyclobutyl group, a cyclopentyl group, and a cyclohexyl group;
a polycyclic cycloalkyl group, including a norbornyl group, an adamantyl group, a tricyclodecyl group, and a tetracyclododecyl group;
a cycloalkenyl group, including a cyclopropenyl group, a cyclobutenyl group, a cyclopentenyl group, and a cyclohexenyl group; and
a polycyclic cycloalkenyl group, including a norbornenyl group, a tricyclodecenyl group, and a tetracyclododecenyl group.

Examples of the monovalent aromatic hydrocarbon group having a carbon number of 6 to 20 include an aryl group, including a phenyl group, a tolyl group, a xylyl group, a naphthyl group, and an anthryl group; and an aralkyl group, including a benzyl group, a phenethyl group, and a naphthylmethyl group.

As $A^{11}$, $A^{12}$, $A^{21}$, $A^{22}$, $A^{31}$ and $A^{32}$ as described above, a hydrogen atom, or a chain hydrocarbon group having a carbon number of 1 to 10 is preferred.

$m^1$, $m^2$ and $m^3$ are each independently an integer of 0 to 5, preferably an integer of 0 to 3, more preferably an integer of 0 to 2, and particularly preferably 0 or 1.

$n^1$, $n^2$ and $n^3$ are each independently an integer of 1 to 4, preferably an integer of 1 to 3, and more preferably 1 or 2.

Examples of the divalent linking group represented by G as described above include an alkanediyl group, a cycloalkanediyl group, an alkenediyl group, arenediyl group, *—$OR^{LA}$—, and *$COOR^{LA}$—. (* refers to a bond to the side of $R^1$.) A part of or all of hydrogen atoms in the group may be substituted with a halogen atom including a fluorine atom or chlorine atom, or a cyano group.

Examples of the alkanediyl group include a methanediyl group, an ethanediyl group, a propanediyl group, a butanediyl group, a hexanediyl group, and an octanediyl group. The alkanediyl group is preferably an alkanediyl group having a carbon number of 1 to 8.

Preferred examples of the cycloalkanediyl group include a cycloalkanediyl group, including a cyclopentanediyl group, and a cyclohexanediyl group; and a polycyclic cycloalkanediyl group, including a norbornane diyl group and an adamantanediyl group. The cycloalkanediyl group is preferably a cycloalkanediyl group having a carbon number of 5 to 12.

Preferred examples of the alkenediyl group include an ethenediyl group, a propenediyl group, and a butenediyl group. The alkenediyl group is preferably an alkenediyl group having a carbon number of 2 to 6.

Examples of the arenediyl group includes a phenylene group, a tolylene group, and a naphthylene group. The arenediyl group is preferably an arenediyl group having carbon number of 6 to 15.

Examples of $R^{LA}$ include the alkanediyl group, the cycloalkanediyl group, the alkenediyl group, and the arenediyl group as each described above.

Preferred examples of the divalent linking group represented by G as described above include a single bond, a methanediyl group, an ethanediyl group, —$COOCH_2$—, and *—$COOCH_2CH_2$—. (* refers to a bond to the side of $R^1$.)

Preferably, each of the molecular weight of an anionic moiety in the radiation-sensitive acid generator is 230 or more. The molecular weight is preferably not more than 600. By adjusting the molecular weight within the ranges, it is possible to control the diffusion length of an acid generated from the radiation-sensitive acid generator to the suitable range, and provide various resist properties at higher level.

The monovalent onium cation represented by $Z_1^+$, $Z_2^+$ and $Z_3^+$ as described above is a cation degradable by irradiating with a radioactive ray. In the exposed part, a sulfonic acid is generated by reacting a proton generated by degradation of the radiation degradable onium cation with the sulfonate anion as described above. Examples of the radioactive ray include ultraviolet ray, far ultraviolet ray, extreme ultraviolet ray (EUV); an electromagnetic wave including X ray and γ ray; an electron beam; and a charged particle radiation such as α ray. Among them, far ultraviolet ray, EUV, or an electron beam is preferred. The far ultraviolet ray is preferably KrF excimer laser light (wavelength is 248 nm) or ArF excimer laser light (wavelength is 193 nm), and more preferably ArF excimer laser light.

Examples of the onium cation include a radiation degradable onium cation, including S, I, O, N, P, Cl, Br, F, As, Se, Sn, Sb, Te, and Bi. Among them, a sulfonium cation having S (sulfur) as an element or an iodonium cation having I (iodine) as an element is preferred, and cations represented by the following formulae (X-1) to (X-5) are more preferred.

[Formula 12]

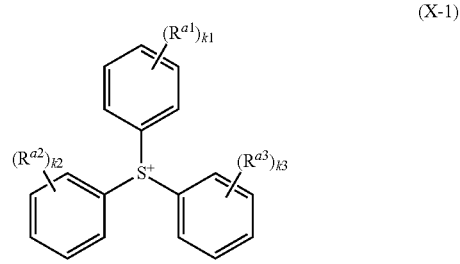

(X-1)

[Formula 13]

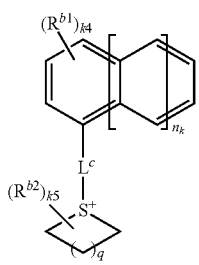
(X-2)

[Formula 14]

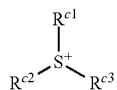
(X-3)

[Formula 15]

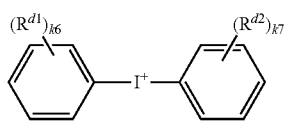
(X-4)

[Formula 16]

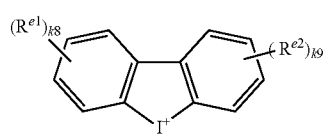
(X-5)

In the above formula (X-1), $R^{a1}$, $R^{a2}$ and $R^{a3}$ are each independently a substituted or unsubstituted, straight or branched chain alkyl group, alkoxy group or alkoxycarbonyloxy group having a carbon number of 1 to 12; a substituted or unsubstituted, monocyclic or polycyclic cycloalkyl group having a carbon number of 3 to 12; a substituted or unsubstituted aromatic hydrocarbon group having a carbon number of 6 to 12; a hydroxy group, —$OSO_2$—$R^P$, —$SO_2$—$R^Q$ or —S—$R^T$; or a ring structure obtained by combining two or more of these groups. $R^P$, $R^Q$ and $R^T$ are each independently a substituted or unsubstituted, straight or branched chain alkyl group having a carbon number of 1 to 12; a substituted or unsubstituted alicyclic hydrocarbon group having a carbon number of 5 to 25; and a substituted or unsubstituted aromatic hydrocarbon group having a carbon number of 6 to 12. k1, k2 and k3 are each independently an integer of 0 to 5. When there are a plurality of $R^{a1}$ to $R^{a3}$ and a plurality of $R^P$, $R^Q$ and $R^T$, a plurality of $R^{a1}$ to $R^{a3}$ and a plurality of $R^P$, $R^Q$ and $R^T$ may be each identical or different.

In the above formula (X-2), $R^{b1}$ is a substituted or unsubstituted, straight chain or branched alkyl group or alkoxy group having a carbon number of 1 to 20; a substituted or unsubstituted acyl group having a carbon number of 2 to 8; or a substituted or unsubstituted aromatic hydrocarbon group having a carbon number of 6 to 8; or a hydroxy group. $n_k$ is 0 or 1. When $n_k$ is 0, k4 is an integer of 0 to 4. When $n_k$ is 1, k4 is an integer of 0 to 7. When there are a plurality of $R^{b1}$, a plurality of $R^{b1}$ may be each identical or different. A plurality of $R^{b1}$ may represent a ring structure obtained by combining them. $R^{b2}$ is a substituted or unsubstituted, straight chain or branched alkyl group having a carbon number of 1 to 7; or a substituted or unsubstituted aromatic hydrocarbon group having a carbon number of 6 to 7. k5 is an integer of 0 to 4. When there are a plurality of $R^{b2}$, a plurality of $R^{b3}$ may be each identical or different. A plurality of $R^{b2}$ may represent a ring structure obtained by combining them. q is an integer of 0 to 3.

In the above formula (X-3), $R^{c1}$, $R^{c2}$ and $R^{c3}$ are each independently a substituted or unsubstituted, straight or branched chain alkyl group having a carbon number of 1 to 12; or a substituted or unsubstituted aromatic hydrocarbon group having a carbon number of 6 to 12.

In the above formula (X-4), $R^{d1}$ and $R^{d2}$ are each independently a substituted or unsubstituted, straight or branched chain alkyl group, alkoxy group or alkoxycarbonyl group having a carbon number of 1 to 12; a substituted or unsubstituted aromatic hydrocarbon group having a carbon number of 6 to 12; a halogen atom; a halogenated alkyl group having a carbon number of 1 to 4; a nitro group; or a ring structure obtained by combining two or more of these groups. k6 and k7 are each independently an integer of 0 to 5. When there are a plurality of $R^{d1}$ and a plurality of $R^{d2}$, a plurality of $R^{d1}$ and a plurality of $R^{d2}$ may be each identical or different.

In the above formula (X-5), $R^{e1}$ and $R^{e2}$ are each independently a halogen atom; a substituted or unsubstituted straight or branched chain alkyl group having a carbon number of 1 to 12; or a substituted or unsubstituted aromatic hydrocarbon group having a carbon number of 6 to 12. k8 and k9 are each independently an integer of 0 to 4.

Examples of a substituent group with which an hydrogen atom in the group as described above may be substituted include a halogen atom, including a fluorine atom, a chlorine atom, a bromine atom, an iodine atom; a hydroxy group, a carboxy group, a cyano group, a nitro group, an alkyl group (when a hydrogen atom in a cycloalkyl group or an aromatic hydrocarbon group is substituted), an aryl group (when a hydrogen atom in an alkyl group is substituted), an alkoxy group, an alkoxycarbonyl group, an alkoxycarbonyloxy group, an acyl group, and an acyloxy group. Among them, a hydroxy group, an alkoxy group, an alkoxycarbonyl group, an alkoxycarbonyloxy group, an acyl group, or an acyloxy group is preferred. An alkoxy group or an alkoxycarbonyl group is more preferred.

Preferably, the compound represented by the above formula (1) is a compound represented by the following formula (1'), the compound represented by the above formula (2) is a compound represented by the following formula (2'), and the compound represented by the above formula (3) is a compound represented by the following formula (3').

[Formula 17]

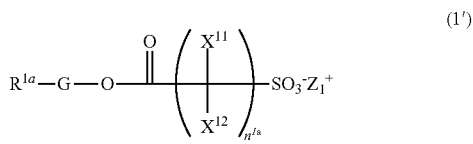
(1')

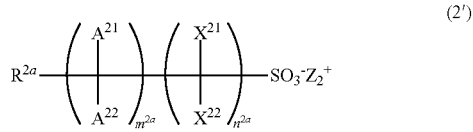
(2')

(3')

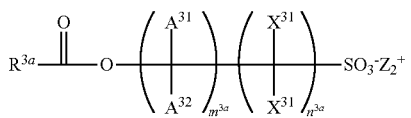

In the formulae (1') to (3'), $R^{1a}$, $R^{2a}$ and $R^{3a}$ are each independently substituted or unsubstituted alicyclic group;

$X^1$, $X^{12}$, $X^{21}$, $X^{22}$, $X^{31}$ and $X^{32}$ are each independently a fluorine atom, or a monovalent fluorinated chain hydrocarbon group having a carbon number of 1 to 10;

$A^{21}$, $A^{22}$, $A^{31}$ and $A^{32}$ are each independently a hydrogen atom, or a chain hydrocarbon group having a carbon number of 1 to 10;

$m^{2a}$ and $m^{3a}$ are each independently 0 or 1;

$n^{1a}$, $n^{2a}$ and $n^{3a}$ are each independently 1 or 2;

G has the same meaning as in the above formula (1); and $Z_1^+$, $Z_2^+$ and $Z_3^+$ each have the same meaning as in the above formulae (1) to (3).

As the alicyclic group, the monovalent fluorinated chain hydrocarbon group having a carbon number of 1 to 10 and the chain hydrocarbon group having a carbon number of 1 to 10, the alicyclic group, the monovalent fluorinated chain hydrocarbon group having a carbon number of 1 to 10 and the chain hydrocarbon group having a carbon number of 1 to 10 in the above formulae (1) to (3) may be suitably applied.

Examples of the compound represented by the above formula (1) include compounds represented by the following formulae (1-1) to (1-10) (hereinafter, also referred as "compounds (1-1) to (1-10)").

[Formula 18]

(1-1)

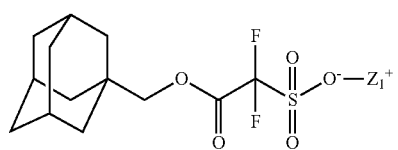

(1-2)

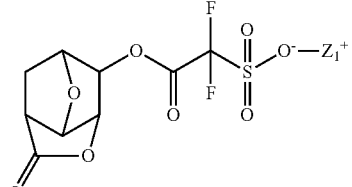

(1-3)

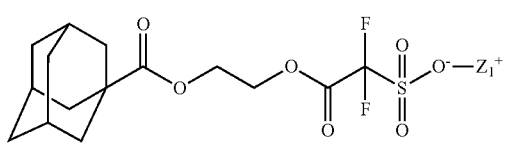

(1-4)

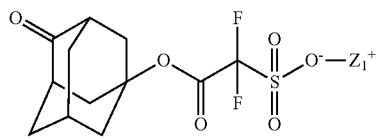

(1-5)

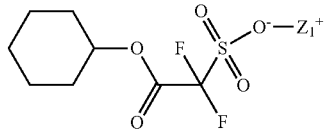

(1-6)

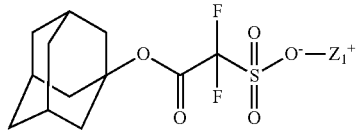

(1-7)

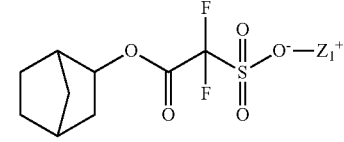

(1-8)

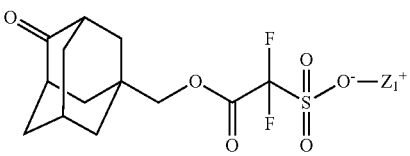

(1-9)

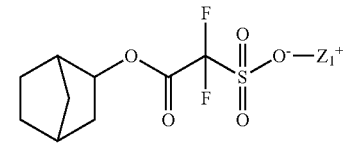

(1-10)

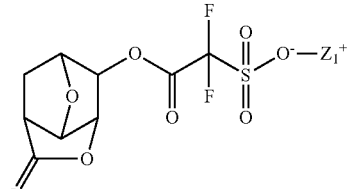

In the above formulae (1-1) to (1-10), Z is a monovalent onium cation.

Among them, compounds (1-1) to (1-5) are preferred as the compound (1).

Examples of the compound represented by the above formula (2) include compounds represented by the following formulae (2-1) to (2-12) (hereinafter, also referred as "compounds (2-1) to (2-12)").

[Formula 19]

(2-1)

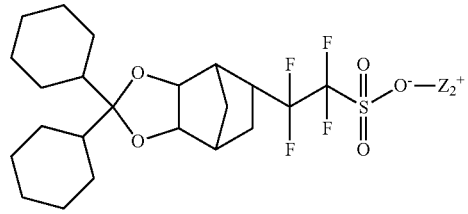

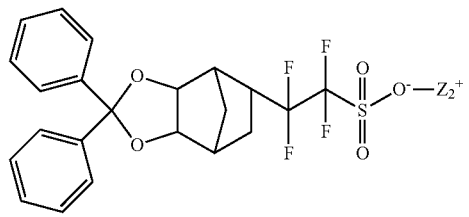 (2-2)
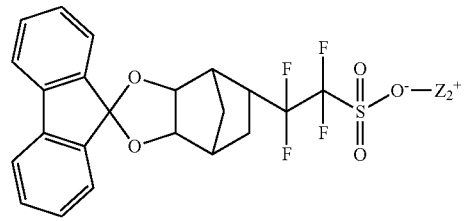 (2-3)
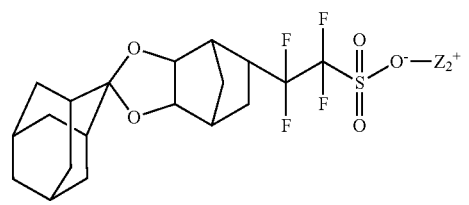 (2-4)
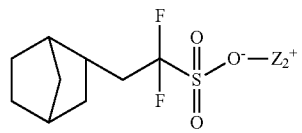 (2-5)
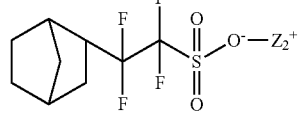 (2-6)
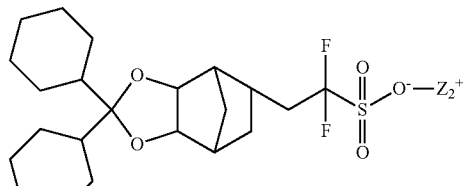 (2-7)
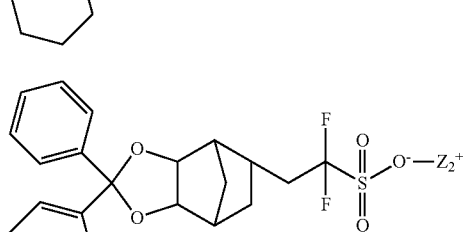 (2-8)
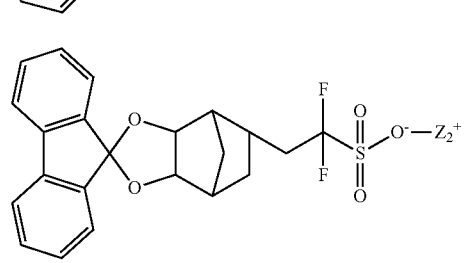 (2-9)
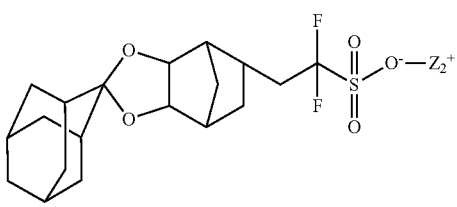 (2-10)
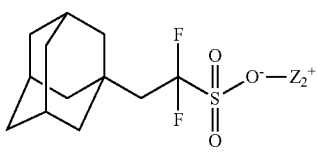 (2-11)
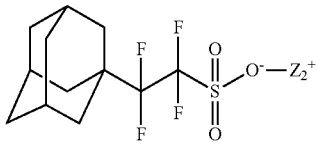 (2-12)
In the above formulae (2-1) to (2-12), $Z_2^*$ is a monovalent onium cation.
Among them, compounds (2-1) to (2-6) are preferred as the compound (2).
Examples of the compound represented by the above formula (3) include compounds represented by the following formulae (3-1) to (3-11) (hereinafter, also referred as "compounds (3-1) to (3-11)").
[Formula 20]
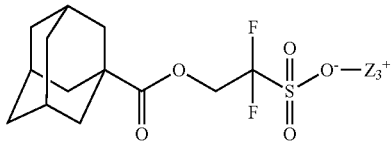 (3-1)
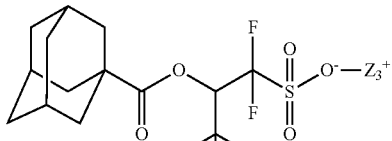 (3-2)
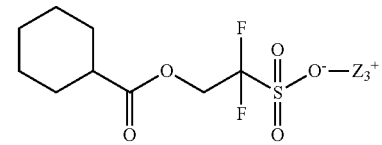 (3-3)
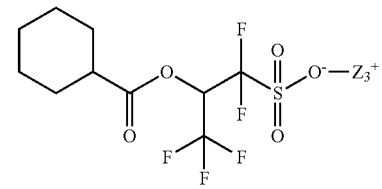 (3-4)

(3-5) 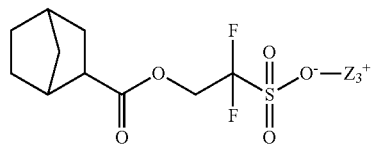

(3-6) 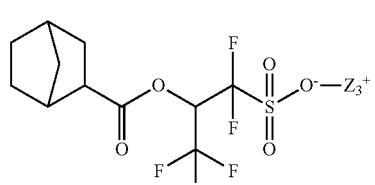

(3-7) 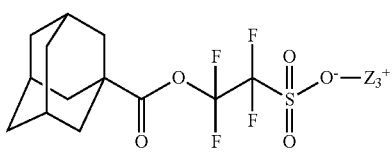

(3-8) 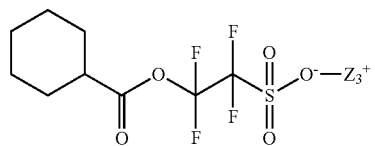

(3-9) 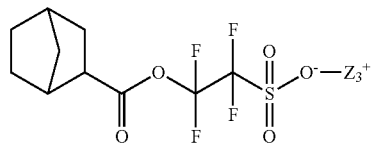

(3-10) 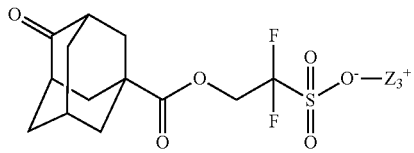

(3-11) 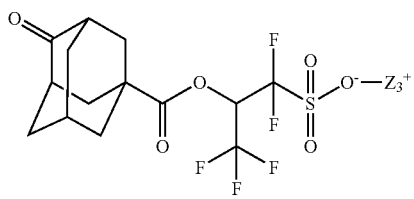

In the above formulae (3-1) to (3-11), $Z_3^+$ is a monovalent onium cation.

Among them, compounds (3-1) to (3-2) are preferred as the compound (3).

Preferably, the radiation-sensitive acid generator is:
the compound represented by the above formula (1) and the compound represented by the above formula (2);
the compound represented by the above formula (1) and the compound represented by the above formula (3); or
the compound represented by the above formula (1), the compound represented by the above formula (2) and the compound represented by the above formula (3).

The various resist properties can be further improved by including at least one of the compounds (2) and (3) as the radiation-sensitive acid generator in addition to the compound (1).

When at least one of the compounds (2) and (3) is included as the radiation-sensitive acid generator in addition to the compound (1), the content of the compound represented by the above formula (1) is preferably not less than 1 part by mass and not more than 45 parts by mass based on 100 parts by mass of total resins. In this case, the lower limit of the content of the compound (1) is more preferably 2 parts by mass, and further preferably 3 parts by mass based on 100 parts by mass of total resins. The upper limit of the content of the compound (1) is more preferably 30 parts by mass, and further preferably 20 parts by mass based on 100 parts by mass of total resins. Thereby, the various resist properties can be improved effectively.

In the radiation-sensitive resin composition of this embodiment, the lower limit of the total content of the radiation-sensitive acid generator is preferably 3 parts by mass, more preferably 5 parts by mass, and further preferably 7 parts by mass based on 100 parts by mass of total base resins. The upper limit of the total content is preferably 45 parts by mass, more preferably 37 parts by mass, and further preferably 35 parts by mass. By adjusting the content of the radiation-sensitive acid generator within the ranges, a resist pattern having improved various resist properties can be formed.

(Synthesis Method of Radiation-Sensitive Acid Generator)

The radiation-sensitive acid generator of this embodiment can be prepared by reacting the corresponding precursor compound (1α) with an alkali metal salt of dithionous acid (for example, sodium salt) in the presence of an inorganic base to form the sulfinic acid salt (2α), oxidizing the sulfinic acid salt with an oxidizing agent such as hydrogen peroxide to form the surfonic acid salt (3α) followed by the ion-exchange reaction with a counter-ion exchange precursor $Z^+Y^-$.

[Formula 21]

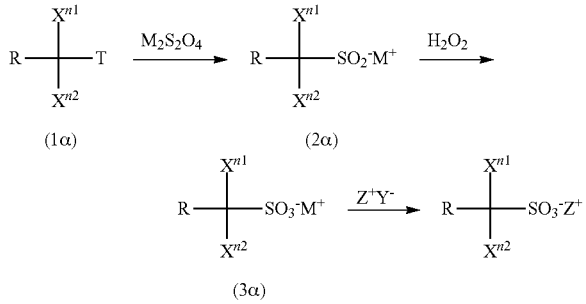

In the above scheme, T is a monovalent leaving group; R is a group corresponding to a structure (including the precursor structure) from the carbon atom on which is substituted with $A^{11}, A^{12}, A^{21}, A^{22}, A^{31}$ and $A^{32}$ in the above formulae (1) to (3) to the ring structure at the terminal; $X^{n1}$ or $X^{n2}$ is a group corresponding to $X^{11}, X^{12}, X^{21}, X^{22}, X^{31}$ and $X^{32}$ in the above formulae (1) to (3); $Z^+$ is a group corresponding to $Z_1^+, Z_2^+$ and $Z_3^+$; and $Y^-$ is a monovalent anion.

(Solvent)

The radiation-sensitive resin composition includes a solvent. The solvent is not particularly limited as long as the solvent can dissolve or disperse at least the resin, the radiation-sensitive acid generator, and optionally an agent such as an acid diffusion controlling agent, if needed.

Examples of the solvent include an alcohol-based solvent, an ether-based solvent, a ketone-based solvent, an amide-based solvent, an ester-based solvent, and a hydrocarbon-based solvent.

Examples of the alcohol-based solvent include:

a monoalcohol-based solvent having a carbon number of 1 to 18, including iso-propanol, 4-methyl-2-pentanol, 3-methoxybutanol, n-hexanol, 2-ethylhexanol, furfuryl alcohol, cyclohexanol, 3,3,5-trimethylcyclohexanol, and diacetone alcohol;

a polyhydric alcohol having a carbon number of 2 to 18, including ethylene glycol, 1,2-propylene glycol, 2-methyl-2,4-pentanediol, 2,5-hexanediol, diethylene glycol, dipropylene glycol, triethylene glycol, and tripropylene glycol; and a partially etherized polyhydric alcohol-based solvent in which a part of hydroxy groups in the polyhydric alcohol-based solvent is etherized.

Examples of the ether-based solvent include:

a dialkyl ether-based solvent, including diethyl ether, dipropyl ether, and dibutyl ether;

a cyclic ether-based solvent, including tetrahydrofuran and tetrahydropyran;

an ether-based solvent having an aromatic ring, including diphenylether and anisole (methyl phenyl ether); and an etherized polyhydric alcohol-based solvent in which a hydroxy group in the polyhydric alcohol-based solvent is etherized.

Examples of the ketone-based solvent include:

a chain ketone-based solvent, including acetone, butanone, and methyl-iso-butyl ketone;

a cyclic ketone-based solvent, including cyclopentanone, cyclohexanone, and methylcyclohexanone; and 2,4-pentanedione, acetonylacetone, and acetophenone.

Examples of the amide-based solvent include:

a cyclic amide-based solvent, including N,N'-dimethyl imidazolidinone and N-methylpyrrolidone; and a chain amide-based solvent, including N-methylformamide, N,N-dimethylformamide, N,N-diethylformamide, acetamide, N-methylacetamide, N,N-dimethylacetamide, and N-methylpropionamide.

Examples of the ester-based solvent include:

a monocarboxylate ester-based solvent, including n-butyl acetate and ethyl lactate;

a partially etherized polyhydric alcohol acetate-based solvent, including diethylene glycol mono-n-butyl ether acetate, propylene glycol monomethyl ether acetate, and dipropylene glycol monomethyl ether acetate;

a lactone-based solvent, including γ-butyrolactone and valerolactone;

a carbonate-based solvent, including diethyl carbonate, ethylene carbonate, and propylene carbonate; and a polyhydric carboxylic acid diester-based solvent, including propylene glycol diacetate, methoxy triglycol acetate, diethyl oxalate, ethyl acetoacetate, ethyl lactate, and diethyl phthalate.

Examples of the hydrocarbon-based solvent include:

an aliphatic hydrocarbon-based solvent, including n-hexane, cyclohexane, and methylcyclohexane;

an aromatic hydrocarbon-based solvent, including benzene, toluene, di-iso-propylbenzene, and n-amylnaphthalene.

Among them, the ester-based solvent or the ketone-based solvent is preferred. The partially etherized polyhydric alcohol acetate-based solvent, the cyclic ketone-based solvent, or the lactone-based solvent is more preferred. Propylene glycol monomethyl ether acetate, cyclohexanone, or γ-butyrolactone is still more preferred. The radiation-sensitive resin composition may include one type of the solvent, or two or more types of the solvents in combination.

(Other Optional Ingredient)

The radiation-sensitive resin composition may also include any other optional ingredient in addition to the ingredients as described above. Examples of the other optional ingredient include an acid diffusion controlling agent, a localization enhancing agent, a surfactant, an alicyclic backbone-containing compound, and a sensitizer.

The other optional ingredient may be used alone, or two or more other optional ingredients may be used in combination.

(Acid Diffusion Controlling Agent)

The radiation-sensitive resin composition may include an acid diffusion controlling agent, if needed. The acid diffusion controlling agent has an effect of controlling the diffusion phenomenon in which an acid resulted from the radiation-sensitive acid generator by the exposure is diffused in the resist film, and of inhibiting undesired chemical reaction in the non-exposed part. The acid diffusion controlling agent can also improve the storage stability of the resulting radiation-sensitive resin composition. The acid diffusion controlling agent can further improve the resolution of the resist pattern and prevent from changing the line width of the resist pattern because of the variation of the pulling and placing time, i.e., the time from the exposure to the developing treatment, and therefore provide the radiation-sensitive resin composition having an improved process stability.

Examples of the acid diffusion controlling agent include a compound represented by the following formula (7) (hereinafter, also referred as a "nitrogen-containing compound (I)"); a compound having two nitrogen atoms in one molecule (hereinafter, also referred as a "nitrogen-containing compound (II)"); a compound having three nitrogen atoms in one molecule (hereinafter, also referred as a "nitrogen-containing compound (III)"); a compound having an amide group; a urea compound; and a nitrogen-containing heterocyclic ring compound.

[Formula 22]

(7)

In the above formula (7), $R^{22}$, $R^{23}$ and $R^{24}$ are each independently a hydrogen atom, a substituted or unsubstituted alkyl group, a substituted or unsubstituted cycloalkyl group, a substituted or unsubstituted aryl group, or a substituted or unsubstituted aralkyl group.

Examples of the nitrogen-containing compound (I) include a monoalkylamine including n-hexylamine; a dialkylamine including di-n-butylamine; a trialkylamine including triethylamine; and an aromatic amine including aniline.

Examples of the nitrogen-containing compound (II) include ethylenediamine and N,N,N',N'-tetramethylethylenediamine.

Examples of the nitrogen-containing compound (III) include a polyamine compound, including polyethyleneimine and polyallylamine; and a polymer including dimethylaminoethylacrylamide.

Examples of the amide-containing compound include formamide, N-methylformamide, N,N-dimethylformamide, acetamide, N-methylacetamide, N,N-dimethylacetamide, propionamide, benzamide, pyrrolidone, and N-methyl pyrrolidone.

Examples of the urea compound include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic ring compound include pyridines, including pyridine and 2-methylpyridine; morpholines, including N-propylmorpholine and N-(undecylcarbonyloxyethyl)morpholine; pyrazine, and pyrazole.

A compound having an acid-dissociable group may be used as the nitrogen-containing organic compound. Examples of the nitrogen-containing organic compound having an acid-dissociable group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-t-butoxycarbonyl-4-hydroxypiperidine, and N-t-amyloxycarbonyl-4-hydroxypiperidine.

A radiation-sensitive weak acid generator from which a weak acid is generated by the exposure may be suitably used as the acid diffusion controlling agent. An acid generated by the radiation-sensitive weak acid generator is a weak acid incapable of inducing dissociation of the acid-dissociable group in a condition that an acid generated by the radiation-sensitive acid generator dissociates the acid-dissociable group in the resin. As used herein, the "dissociation" of the acid-dissociable group means that the group is dissociated during the post-exposure bake at 110° C. for 60 seconds.

Example of the radiation-sensitive weak acid generator includes an onium salt compound in which the compound is degraded by the exposure to lose the acid diffusion controlling properties. Examples of the onium salt compound include a sulfonium salt compound represented by the following formula (8-1), and an iodonium salt compound represented by the following formula (8-2).

[Formula 23]

$$J^+E^- \quad (8\text{-}1)$$

$$U^+Q^- \quad (8\text{-}2)$$

In the above formula (8-1) and formula (8-2), $J^+$ is a sulfonium cation; and $U^+$ is an iodonium cation. Examples of the sulfonium cation represented by $J^+$ include sulfonium cations represented by the above formulae (X-1) to (X-3). Examples of the iodonium cation represented by $U^+$ include iodonium cations represented by the above formulae (X-4) to (X-5). $E^-$ and $Q^-$ are each independently anion represented by $OH^-$, $R^\alpha$—$COO^-$, and $R^\alpha$—$SO_3^-$. $R^\alpha$ is an alkyl group, an aryl group, or an aralkyl group. A hydrogen atom in the aromatic ring of the aryl group or the aralkyl group represented by $R^\alpha$ may be substituted with a hydroxy group, a fluorine atom-substituted or unsubstituted alkyl group having a carbon number of 1 to 12, or an alkoxy group having a carbon number of 1 to 12.

Examples of the radiation-sensitive weak acid generator include compounds represented by the following formulae.

[Formula 24]

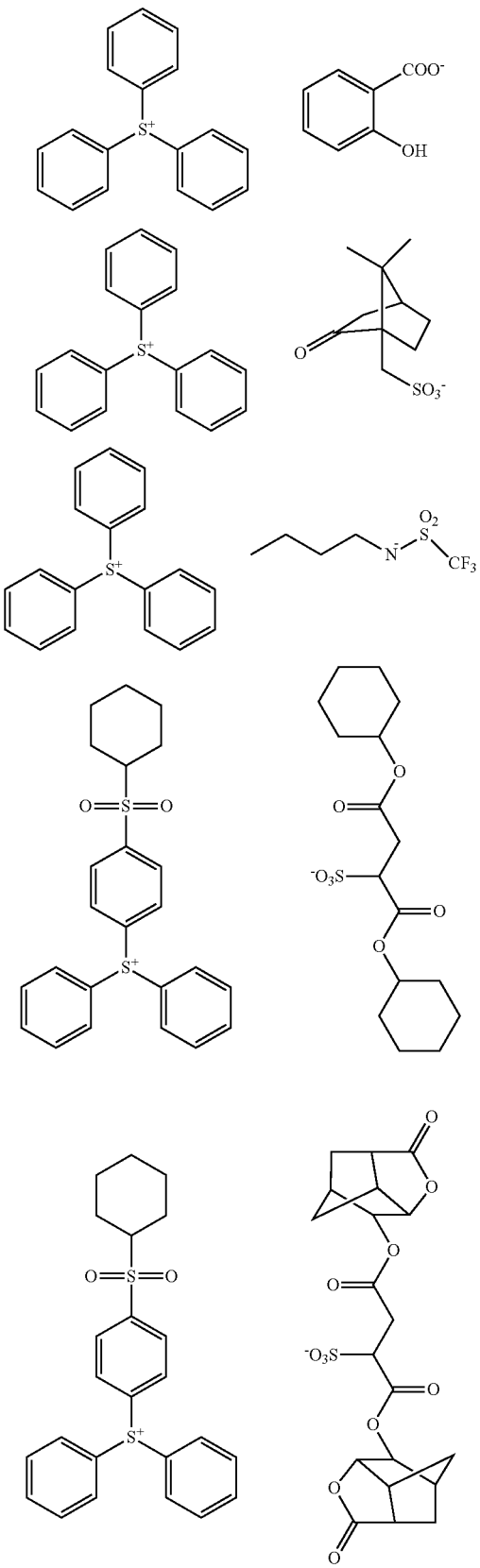

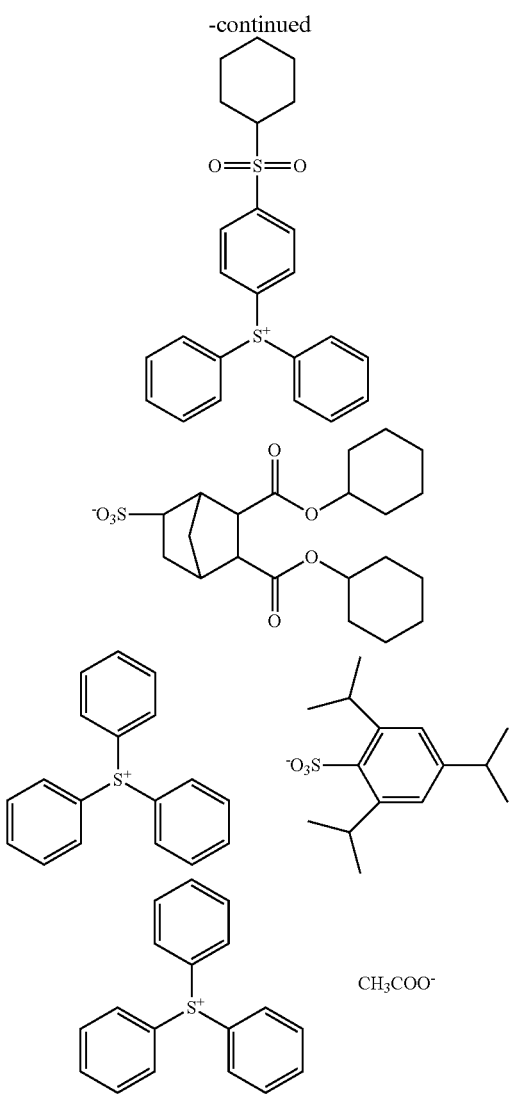

Among them, the radiation-sensitive weak acid generator is preferably the sulfonium salt, more preferably a triarylsulfonium salt, and further preferably a triphenylsulfonium salicylate or triphenylsulfonium 10-camphorsulfonate.

The lower limit of the content of the acid diffusion controlling agent is preferably 3 parts by mass, more preferably 4 parts by mass, and further preferably 5 parts by mass based on 100 parts by mass of total radiation-sensitive acid generators. The upper limit of the content is preferably 150 parts by mass, more preferably 120 parts by mass, and further preferably 110 parts by mass.

By adjusting the content of the acid diffusion controlling agent within the ranges, the radiation-sensitive resin composition can provide improved lithography properties. The radiation-sensitive resin composition may contain one type of the acid diffusion controlling agent, or two or more acid diffusion controlling agents in combination.

(Localization Enhancing Agent)

The localization enhancing agent has an effect of localizing the high fluorine-containing resin on the surface of the resist film more effectively. The added amount of the high fluorine-containing resin can be decreased compared to the traditionally added amount by including the localization enhancing agent in the radiation-sensitive resin composition. The localization enhancing agent can further prevent from eluting the ingredient of the composition from the resist film to an immersion medium and carry out the immersion exposure at higher speed with a high-speed scan, while maintaining the lithography properties of the radiation-sensitive resin composition. As a result, the hydrophobicity of the surface of the resist film can be improved, resulting in the prevention of the defect due to the immersion, for example, the watermark defect. Example of the compound which may be used as the localization enhancing agent includes a low molecular weight compound having a specific dielectric constant of not less than 30 and not more than 200 and a boiling point of 100° C. or more at 1 atm. Specific examples of the compound include a lactone compound, a carbonate compound, a nitrile compound, and a polyhydric alcohol.

Examples of the lactone compound include γ-butyrolactone, valerolactone, mevaloniclactone, and norbornane lactone.

Examples of the carbonate compound include propylene carbonate, ethylene carbonate, butylene carbonate, and vinylene carbonate.

Example of the nitrile compound includes succinonitrile.

Example of the polyhydric alcohol includes glycerine.

The lower limit of the content of the localization enhancing agent is preferably 10 parts by mass, more preferably 15 parts by mass, further preferably 20 parts by mass, and more further preferably 25 parts by mass based on 100 parts by mass of total resins in the radiation-sensitive resin composition. The upper limit of the content is preferably 300 parts by mass, more preferably 200 parts by mass, further preferably 100 parts by mass, and more further preferably 80 parts by mass. The radiation-sensitive resin composition may include one type of the localization enhancing agent, or two or more types of localization enhancing agents in combination.

(Surfactant)

The surfactant has an effect of improving the coating properties, the striation, and the developability of the composition. Examples of the surfactant include a nonionic surfactant, including polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate. Examples of the surfactant which is commercially available include KP341 (manufactured by Shin-Etsu Chemical Co., Ltd.), POLYFLOW No. 75, POLYFLOW No. 95 (all manufactured by Kyoeisha Chemical Co., Ltd.), EFTOP EF301, EFTOP EF303, EFTOP EF352 (all manufactured by Tokem Products), Megafac F171, Megafac F173 (all manufactured by DIC), Fluorad FC430, Fluorad FC431 (all manufactured by Sumitomo 3M Limited.), AsahiGuard AG710, Surflon S-382, Surflon SC-101, Surflon SC-102, Surflon SC-103, Surflon SC-104, Surflon SC-105, Surflon SC-106 (all manufactured by Asahi Glass Co., Ltd.). The content of the surfactant in the radiation-sensitive resin composition is typically not more than 2 parts by mass based on 100 parts by mass of total resins.

(Alicyclic Backbone-Containing Compound)

The alicyclic backbone-containing compound has an effect of improving the dry etching resistance, the shape of the pattern, the adhesiveness between the substrate, and the like.

Examples of the alicyclic backbone-containing compound include:

adamantane derivatives, including 1-adamantane carboxylic acid, 2-adamantanone, and t-butyl 1-adamantane carboxylate;

deoxycholic acid esters, including t-butyl deoxycholate, t-butoxycarbonylmethyl deoxycholate, and 2-ethoxyethyl deoxycholate;

lithocholic acid esters, including t-butyl lithocholate, t-butoxycarbonylmethyl lithocholate, and 2-ethoxyethyl lithocholate; and 3-[2-hydroxy-2,2-bis(trifluoromethyl)ethyl]tetra cyclo [4.4.0.1 2,5.17,10]dodecane, and 2-hydroxy-9-methoxycarbonyl-5-oxo-4-oxa-tricyclo[4.2.1.03,7]nonane. The content of the alicyclic backbone-containing compound in the radiation-sensitive resin composition is typically not more than 5 parts by mass based on 100 parts by mass of total resins.

(Sensitizer)

The sensitizer shows an action of increasing the production of the acid, for example, from the radiation-sensitive acid generator, and has an effect of improving the "apparent sensitivity" of the radiation-sensitive resin composition.

Examples of the sensitizer include carbazoles, acetophenones, benzophenones, naphthalenes, phenols, biacetyl, eosin, rose bengal, pyrenes, anthracenes, and phenothiazines. The sensitizer may be used alone, or two or more sensitizers may be used in combination. The content of the sensitizer in the radiation-sensitive resin composition is typically not more than 2 parts by mass based on 100 parts by mass of total resins.

<Method for Preparing Radiation-Sensitive Resin Composition>

For example, the radiation-sensitive resin composition can be prepared by mixing the resin, the radiation-sensitive acid generator, optionally the acid diffusion controlling agent, the high fluorine-containing resin, and the solvent in a predetermined ratio. After mixing, the radiation-sensitive resin composition is preferably filtered, for example, through a membrane filter having a pore size of about 0.05 µm. The solid concentration of the radiation-sensitive resin composition is typically from 0.1% by mass to 50% by mass, preferablly from 0.5% by mass to 30% by mass, and more preferably from 1% by mass to 20% by mass.

<Method for Forming Resist Pattern>

The method for forming a resist pattern includes the steps of:

forming a resist film from the radiation-sensitive resin composition (hereinafter, also referred as a "resist film forming step");

exposing the resist film (hereinafter, also referred as a "exposing step"); and developing the exposed resist film (hereinafter, also referred as a "developing step").

According to the method for forming a resist pattern, the resist pattern can be formed having an improved resolution, the rectangularity of the cross-section shape, LWR properties, depth of focus, MEEF properties, and the shrinkage control of the resist film during PEB. Each steps will be described below.

[Resist Film Forming Step]

In this step, a resist film is formed from the radiation-sensitive resin composition. Examples of the substrate on which the resist film is formed include one traditionally known in the art, including a silicon wafer, silicon dioxide, and a wafer coated with aluminum. An organic or inorganic antireflection film may be formed on the substrate, as disclosed in JP-B-06-12452 and JP-A-59-93448. Examples of the applicating method include a rotary coating (spin coating), flow casting, and roll coating. After applicating, a prebake (PB) may be carried out in order to evaporate the solvent in the film, if needed. The temperature of PB is typically from 60° C. to 140° C., and preferably from 80° C. to 120° C. The duration of PB is typically from 5 seconds to 600 seconds, and preferably from 10 seconds to 300 seconds. The thickness of the resist film formed is preferably from 10 nm to 1,000 nm, and more preferably from 10 nm to 500 nm.

When the immersion exposure is carried out, irrespective of presence of a water repellent polymer additive such as the high fluorine-containing resin in the radiation-sensitive resin composition, the formed resist film may have a protective film for the immersion which is not soluble into the immersion liquid on the film in order to prevent a direct contact between the immersion liquid and the resist film. As the protective film for the immersion, a solvent-removable protective film that is removed with a solvent before the developing step (for example, see JP-A-2006-227632); or a developer-removable protective film that is removed during the development of the developing step (for example, see WO2005-069076 and WO2006-035790) may be used. In terms of the throughput, the developer-removable protective film is preferably used.

When the subsequent exposing step is carried out by a radiation having a wavelength of 50 nm or less, the resin having the structure units (I) and (III) as the base resin is preferably used in the composition.

[Exposing Step]

In this step, the resist film formed in the resist film forming step is exposed by irradiating with a radioactive ray through a photomask (optionally through an immersion medium such as water). Examples of the radioactive ray used for the exposure include visible ray, ultraviolet ray, far ultraviolet ray, extreme ultraviolet ray (EUV); an electromagnetic wave including X ray and γ ray; an electron beam; and a charged particle radiation such as α ray. Among them, far ultraviolet ray, an electron beam, or EUV is preferred. ArF excimer laser light (wavelength is 193 nm), KrF excimer laser light (wavelength is 248 nm), an electron beam, or EUV is more preferred. An electron beam or EUV having a wavelength of 50 nm or less which is identified as the next generation exposing technology is further preferred.

When the exposure is carried out by immersion exposure, examples of the immersion liquid include water and fluorine-based inert liquid. The immersion liquid is preferably a liquid which is transparent with respect to the exposing wavelength, and has a minimum temperature factor of the refractive index so that the distortion of the light image reflected on the film becomes minimum. However, when the exposing light source is ArF excimer laser light (wavelength is 193 nm), water is preferably used because of the ease of availability and ease of handling in addition to the above considerations. When water is used, a small proportion of an additive that decreases the surface tension of water and increases the surface activity may be added. Preferably, the additive can not dissolve the resist film on the wafer and can neglect an infuence on an optical coating at an under surface of a lens. The water used is preferably distilled water.

After the exposure, post exposure bake (PEB) is preferably carried out to promote the dissociation of the acid-dissociable group in the resin by the acid generated from the radiation-sensitive acid generator with the exposure in the exposed part of the resist film. The difference of solubility into the developer between the exposed part and the non-exposed part is generated by the PEB. The temperature of PEB is typically from 50° C. to 180° C., and preferably from 80° C. to 130° C. The duration of PEB is typically from 5 seconds to 600 seconds, and preferably from 10 seconds to 300 seconds.

[Developing Step]

In this step, the resist film exposed in the exposing step is developed. By this step, the predetermined resist pattern can be formed. After the development, the resist pattern is washed with a rinse solution such as water or alcohol, and the dried, in general.

Examples of the developer used for the development include, in the alkaline development, an alkaline aqueous solution obtained by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethyl ammonium hydroxide (TMAH), pyrrole, piperidine, choline, 1,8-diazabicyclo-[5.4.0]-7-undecene, 1,5-diazabicyclo-[4.3.0]-5-nonene. Among them, an aqueous TMAH solution is preferred, and 2.38% by mass of aqueous TMAH solution is more preferred.

In the case of the development with organic solvent, examples of the solvent include an organic solvent, including a hydrocarbon-based solvent, an ether-based solvent, an ester-based solvent, a ketone-based solvent, and an alcohol-based solvent; and a solvent containing an organic solvent. Examples of the organic solvent include one, two or more solvents listed as the solvent for the radiation-sensitive resin composition. Among them, an ester-based solvent or a ketone-based solvent is preferred. The ester-based solvent is preferably an acetate ester-based solvent, and more preferably n-butyl acetate or amyl acetate. The ketone-based solvent is preferably a chain ketone, and more preferably 2-heptanone. The content of the organic solvent in the developer is preferably not less than 80% by mass, more preferably not less than 90% by mass, further preferably not less than 95% by mass, and particularly preferably not less than 99% by mass. Examples of the ingredient other than the organic solvent in the developer include water and silicone oil.

Examples of the developing method include a method of dipping the substrate in a tank filled with the developer for a given time (dip method); a method of developing by putting and leaving the developer on the surface of the substrate with the surface tension for a given time (paddle method); a method of spraying the developer on the surface of the substrate (spray method); and a method of injecting the developer while scanning an injection nozzle for the developer at a constant rate on the substrate rolling at a constant rate (dynamic dispense method).

EXAMPLES

Although the present invention will be specifically described with reference to Examples, it is not intended that the present invention is limited to these Examples.

The measurement method for various properties will be described below.

[Measurement of Weight Average Molecular Weight (Mw), Number Average Molecular Weight (Mn) and Dispersity (Mw/Mn)]

The Mw and Mn of the resin were measured by Gel Permeation Chromatography (GPC) with GPC columns from Tosoh Corporation (two G2000HXLs, one G3000HXL, and one G4000HXL) under the condition as described below. The dispersity (Mw/Mn) was calculated by the measurement results of Mw and Mn.

Eluting Solvent: tetrahydrofuran
Flow Rate: 1.0 mL/min
Sample Concentration: 1.0% by mass
Sample Injection Amount: 100 μL
Column Temperature: 40° C.
Detector: differential refractometer
Reference Material: monodisperse polystyrene

[$^1$H-NMR Analysis and $^{13}$C-NMR Analysis]

The content by percent (mol %) of each structure units in each resins was analyzed by using "JNM-Delta400" manufactured by JEOL Ltd.

<Synthesis of Base Resin and High Fluorine-Containing Resin>

The compounds (M-1) to (M-5) as described below were used as monomers which were used for the synthesis of each resins in each Examples and each Comparative Examples. It is noted that in the Synthesis Examples, parts by mass means an amount assuming that total mass of the used monomers is 100 parts by mass, and that mol % means an amount assuming that total mole numbers of the used monomers is 100 mol %, unless otherwise specified.

[Formula 25]

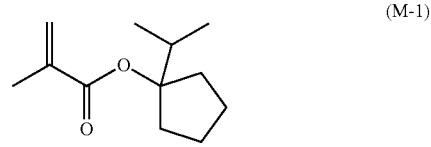

(M-1)

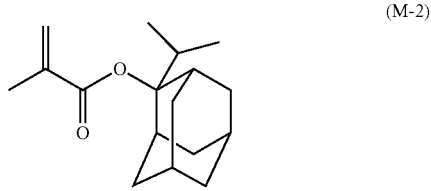

(M-2)

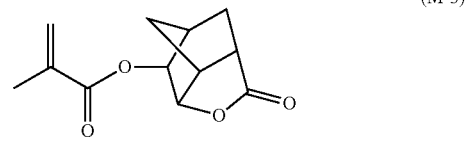

(M-3)

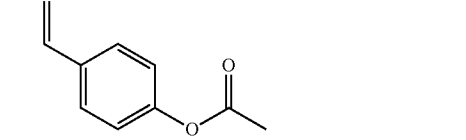

(M-4)

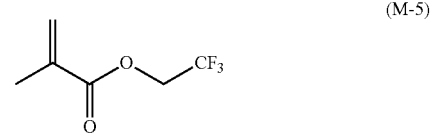

(M-5)

Synthesis Example 1

(Synthesis of Base Resin (A-1))

The compound (M-1), the compound (M-2) and the compound (M-3) as monomers were dissolved in 2-butanone (200 parts by mass) at molar ratio of 40/10/50. AIBN (5 mol %) was added as an initiator to prepare a monomer solution. To a reactor was added 2-butanone (100 parts by mass), and the reactor was purged with nitrogen gas for 30 minutes. The temperature in the reactor was set at 80° C., and the monomer solution was added dropwise to the reactor under agitation for 3 hours. The start of the addition was regarded as the start time of the polymerization reaction, and the polymerization reaction was continued for 6 hours. After completing the polymerization reaction, the polymer solution was cooled to 30° C. or less by cooling with water. The cooled polymer solution was poured to methanol (2,000 parts by mass). The precipitated white powder was filtered. The filtered white powder was washed with methanol twice, filtered, and dried at 50° C. for 17 hours to obtain a base resin (A-1) as white powder in good yield. The Mw of the base resin (A-1) was 7,800, and the Mw/Mn was 1.41. As a result of $^{13}$C-NMR analysis, the content by percent of each structure unit derived from the compounds (M-1), (M-2) and (M-3) was 40.2 mol %, 9.1 mol % and 50.7 mol %, respectively.

Synthesis Example 2

(Synthesis of Base Resin (A-2))

The compound (M-1), the compound (M-2) and the compound (M-4) as monomers were dissolved in propylene glycol monomethyl ether (100 parts by mass) at molar ratio of 40/10/50. AIBN (6 mol %) as an initiator and t-dodecyl mercaptan (38 parts by mass per 100 parts by mass of the initiator) as a chain transfer agent was added to prepare a monomer solution. The monomer solution was subjected to copolymerization under nitrogen atmosphere for 16 hours while maintaining the reaction temperature at 70° C. After completing the polymerization reaction, the polymer solution was added dropwise in n-hexane (1,000 parts by mass) and the polymer was solidified and purified. To the polymer was added propylene glycol monomethyl ether (150 parts by mass) additionally. Further, methanol (150 parts by mass), triethylamine (1.5 molar equivalent based on the used amount of the compound (M-4)) and water (1.5 molar equivalent based on the used amount of the compound (M-4)) were added, and hydrolyzed for 8 hours while refluxing at the boiling point. After completing the reaction, the solvent and triethylamine were evaporated under reduced pressure. The resulting polymer was dissolved in acetone (150 parts by mass), and added dropwize in water (2,000 parts by mass) to solidify the polymer. The resulting white powder was filtered. The white powder was dried at 50° C. for 17 hours to obtain a base resin (A-2) as white powder in good yield. The Mw of the base resin (A-2) was 6,000, and the Mw/Mn was 1.81. As a result of $^{13}$C-NMR analysis, the content by percent of each structure unit derived from the compounds (M-1), (M-2) and (M-4) was 41.3 mol %, 8.0 mol % and 50.7 mol %, respectively.

Synthesis Example 3

(Synthesis of High Fluorine-Containing Resin (D-1))

The compound (M-1) and the compound (M-5) as monomers were dissolved in 2-butanone (200 parts by mass) at molar ratio of 70/30. AIBN (5 mol % based on the total monomers) was added as an initiator to prepare a monomer solution. To a reactor was added 2-butanone (100 parts by mass), and the reactor was purged with nitrogen gas for 30 minutes. The temperature in the reactor was set at 80° C., the monomer solution was added dropwise to the reactor under agitation for 3 hours. The start of the addition was regarded as the start time of the polymerization reaction, and the polymerization reaction was continued for 6 hours. After completing the polymerization reaction, the polymer solution was cooled to 30° C. or less by cooling with water. The solvent was replaced with acetonitrile (400 parts by mass). Hexane (100 parts by mass) was added and stirred, and the acetonitrile layer was collected. The collection was repeated three times in total. By replacing the solvent with propylene glycol monomethyl ether acetate, a solution of the high fluorine-containing resin (D-1) was obtained in good yield. The Mw of the polymer (D-1) was 7,300, and the Mw/Mn was 2.00. As a result of $^{13}$C-NMR analysis, the content by percent of each structure unit derived from the compounds (M-1) and (M-5) was 71.1 mol % and 28.9 mol %, respectively.

The content by percent, the Mw and the Mw/Mn of each structure units in the resulting resin are shown in Table 1. It is noted that "—" in the following table means that the corresponding ingredient is not used.

TABLE 1

| | | Monomer 1 | | Monomer 2 | | Monomer 3 | | | |
| --- | --- | --- | --- | --- | --- | --- | --- | --- | --- |
| | Resin | Type | Used amount (mol %) | Type | Used amount (mol %) | Type | Used amount (mol %) | Mw | Mw/Mn |
| Synthesis Example 1 | A-1 | M-1 | 40 | M-2 | 10 | M-3 | 50 | 7,800 | 1.41 |
| Synthesis Example 2 | A-2 | M-1 | 40 | M-2 | 10 | M-4* | 50 | 6,000 | 1.81 |
| Synthesis Example 3 | D-1 | M-1 | 70 | — | — | M-5 | 30 | 7,300 | 2.00 |

*In the base resin (A-2), it is presented as p-hydroxystyrene structure unit derived from the compound (M-4).

<Preparation of Radiation-Sensitive Resin Composition>

Ingredients other than the base resin and the high fluorine-containing resin will now be described as the components of the radiation-sensitive resin composition.

(Radiation-Sensitive Acid Generator)

The compounds represented by the following formulae (1-1) to (1-5), (2-1) to (2-6) and (3-1) to (3-2) (hereinafter, also referred as a "compound (1-1)" and the like) were used as the radiation-sensitive acid generator.
[Formula 26]
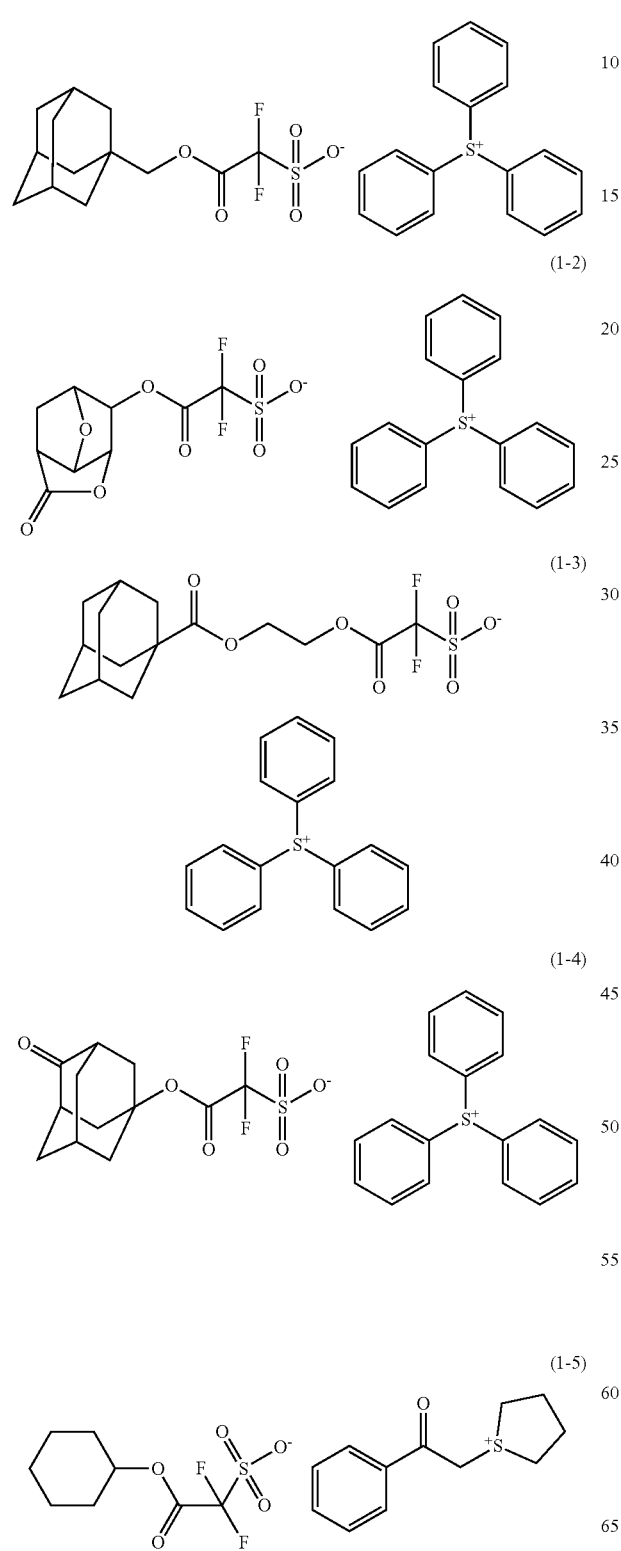
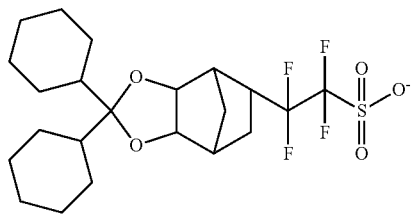
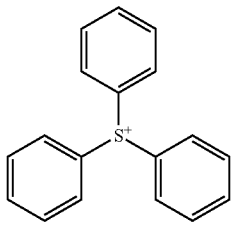
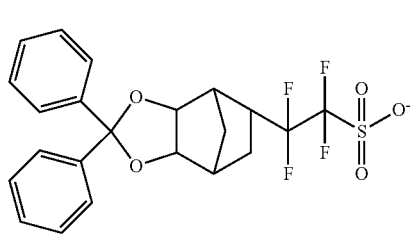
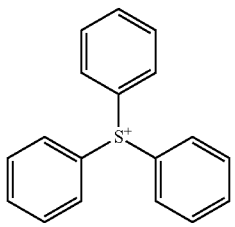 [SMILES: c1ccc([S+](c2ccccc2)c2ccccc2)cc1]
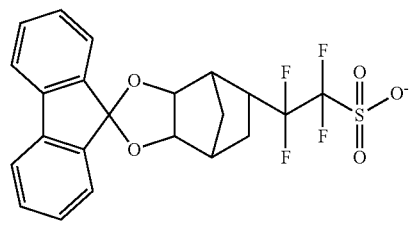
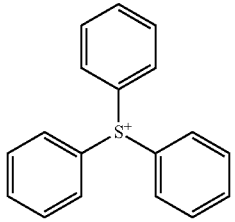
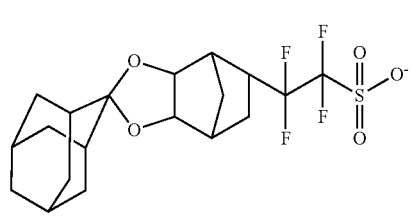

-continued

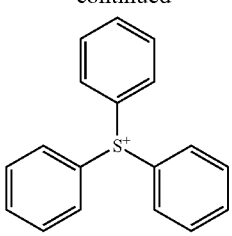
(2-5)

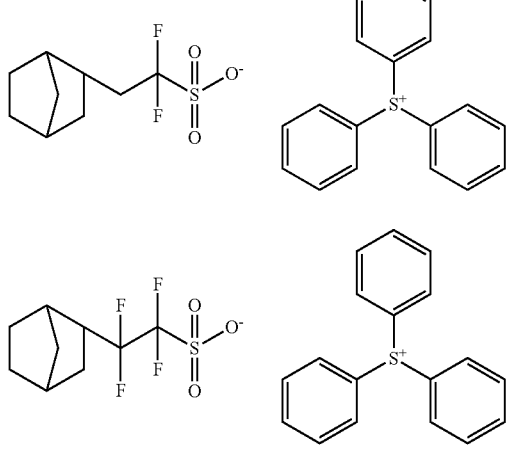
(2-6)

(3-1)

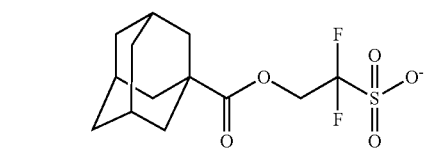

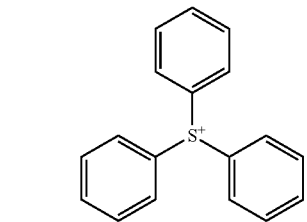

(3-2)

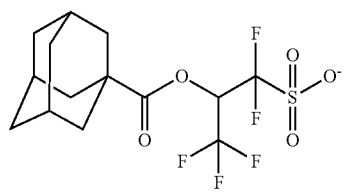

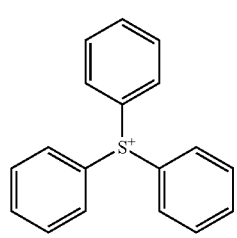

(Acid Diffusion Controlling Agent)

The compounds represented by the following formulae (C-1) to (C-3) (hereinafter, also referred as a "compound (C-1)" and the like) were used as the acid diffusion controlling agent.

[Formula 27]

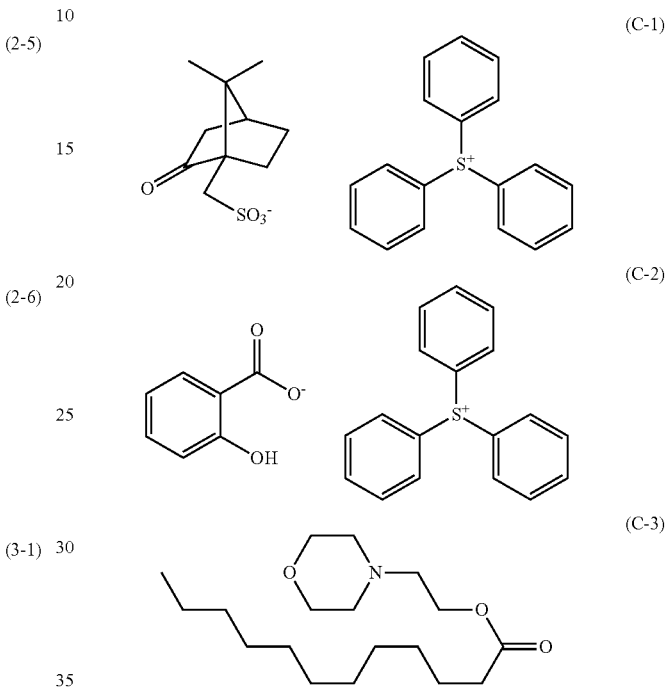

(Solvent)

The following (E-1) to (E-4) were used as the solvent.

E-1: propylene glycol monomethyl ether acetate
E-2: cyclohexanone
E-3: γ-butyrolactone
E-4: ethyl lactate Example 1

The radiation-sensitive resin composition (J-1) was prepared by mixing 100 parts by mass of the base resin (A-1), 5 parts by mass of the compound (1-1) and 5 parts by mass of the compound (2-1) as the radiation-sensitive acid generator, 7 parts by mass of the compound (C-1) as the acid diffusion controlling agent, 3 parts by mass of the high fluorine-containing resin (D-1), and 2,240 parts by mass of (E-1), 960 parts by mass of (E-2) and 30 parts by mass of (E-3) as the solvent, and then filtering through a membrane filter having a pore size of 0.2 μm.

Examples 2-20 and Comparative Examples 1-7

The radiation-sensitive resin compositions (J-2) to (J-20) and (K-1) to (K-7) were prepared by using the method similar as in Example 1, except that the type and content of each ingredients as shown in Table 2 were used.

TABLE 2

| Radiation-sensitive resin composition | Base resin | | Radiation-sensitive acid generator | | | | Acid diffusion controlling agent | | High fluorine-containing resin | | Solvent | |
|---|---|---|---|---|---|---|---|---|---|---|---|---|
| | Type | Content (Parts by mass) | Type | Content (Parts by mass) | Type | Content (Parts by mass) | Type | Content (Parts by mass) | Type | Content (Parts by mass) | Type | Content (Parts by mass) |
| Example 1 | J-1 | A-1 | 100 | 1-1 | 5 | 2-1 | 5 | C-1 | 7 | D-1 | 3 | E-1/E-2/E-3 | 2240/960/30 |
| Example 2 | J-2 | A-1 | 100 | 1-1 | 5 | 2-2 | 5 | C-1 | 7 | D-1 | 3 | E-1/E-2/E-3 | 2240/960/30 |
| Example 3 | J-3 | A-1 | 100 | 1-1 | 5 | 2-3 | 5 | C-2 | 7 | D-1 | 3 | E-1/E-2/E-3 | 2240/960/30 |
| Example 4 | J-4 | A-1 | 100 | 1-1 | 5 | 2-4 | 5 | C-1 | 7 | D-1 | 3 | E-1/E-2/E-3 | 2240/960/30 |
| Example 5 | J-5 | A-1 | 100 | 1-1 | 5 | 2-5 | 5 | C-1 | 7 | D-1 | 3 | E-1/E-2/E-3 | 2240/960/30 |
| Example 6 | J-6 | A-1 | 100 | 1-1 | 5 | 2-6 | 5 | C-1 | 7 | D-1 | 3 | E-1/E-2/E-3 | 2240/960/30 |
| Example 7 | J-7 | A-1 | 100 | 1-1 | 5 | 3-1 | 5 | C-1 | 7 | D-1 | 3 | E-1/E-2/E-3 | 2240/960/30 |
| Example 8 | J-8 | A-1 | 100 | 1-1 | 5 | 3-2 | 5 | C-3 | 4 | D-1 | 3 | E-1/E-2/E-3 | 2240/960/30 |
| Example 9 | J-9 | A-1 | 100 | 1-1 | 5 | 2-1 | 5 | C-3 | 4 | D-1 | 3 | E-1/E-2/E-3 | 2240/960/30 |
| Example 10 | J-10 | A-1 | 100 | 1-2 | 5 | 3-1 | 5 | C-1 | 7 | D-1 | 3 | E-1/E-2/E-3 | 2240/960/30 |
| Example 11 | J-11 | A-1 | 100 | 1-2 | 5 | 2-1 | 5 | C-2 | 7 | D-1 | 3 | E-1/E-2/E-3 | 2240/960/30 |
| Example 12 | J-12 | A-1 | 100 | 1-3 | 5 | 3-1 | 5 | C-1 | 7 | D-1 | 3 | E-1/E-2/E-3 | 2240/960/30 |
| Example 13 | J-13 | A-1 | 100 | 1-4 | 5 | 2-1 | 5 | C-3 | 4 | D-1 | 3 | E-1/E-2/E-3 | 2240/960/30 |
| Example 14 | J-14 | A-1 | 100 | 2-1 | 5 | 3-1 | 5 | C-1 | 7 | D-1 | 3 | E-1/E-2/E-3 | 2240/960/30 |
| Example 15 | J-15 | A-1 | 100 | 2-2 | 5 | 3-1 | 5 | C-1 | 7 | D-1 | 3 | E-1/E-2/E-3 | 2240/960/30 |
| Example 16 | J-16 | A-1 | 100 | 2-3 | 5 | 3-1 | 5 | C-1 | 7 | D-1 | 3 | E-1/E-2/E-3 | 2240/960/30 |
| Example 17 | J-17 | A-1 | 100 | 2-4 | 5 | 3-1 | 5 | C-1 | 7 | D-1 | 3 | E-1/E-2/E-3 | 2240/960/30 |
| Example 18 | J-18 | A-1 | 100 | 2-5 | 5 | 3-1 | 5 | C-1 | 7 | D-1 | 3 | E-1/E-2/E-3 | 2240/960/30 |
| Example 19 | J-19 | A-1 | 100 | 2-6 | 5 | 3-2 | 5 | C-1 | 7 | D-1 | 3 | E-1/E-2/E-3 | 2240/960/30 |
| Example 20 | J-20 | A-1 | 100 | 2-1 | 5 | 3-1 | 5 | C-3 | 4 | D-1 | 3 | E-1/E-2/E-3 | 2240/960/30 |
| Comparative example 1 | K-1 | A-1 | 100 | 1-1 | 5 | 1-2 | 5 | C-1 | 7 | D-1 | 3 | E-1/E-2/E-3 | 2240/960/30 |
| Comparative example 2 | K-2 | A-1 | 100 | 2-1 | 5 | 2-6 | 5 | C-1 | 7 | D-1 | 3 | E-1/E-2/E-3 | 2240/960/30 |
| Comparative example 3 | K-3 | A-1 | 100 | 3-1 | 5 | 3-2 | 5 | C-1 | 7 | D-1 | 3 | E-1/E-2/E-3 | 2240/960/30 |
| Comparative example 4 | K-4 | A-1 | 100 | 1-1 | 10 | — | — | C-2 | 7 | D-1 | 3 | E-1/E-2/E-3 | 2240/960/30 |
| Comparative example 5 | K-5 | A-1 | 100 | 1-5 | 10 | — | — | C-1 | 7 | D-1 | 3 | E-1/E-2/E-3 | 2240/960/30 |
| Comparative example 6 | K-6 | A-1 | 100 | 2-6 | 10 | — | — | C-1 | 7 | D-1 | 3 | E-1/E-2/E-3 | 2240/960/30 |
| Comparative example 7 | K-7 | A-1 | 100 | 3-1 | 10 | — | — | C-1 | 7 | D-1 | 3 | E-1/E-2/E-3 | 2240/960/30 |

<Formation of Resist Pattern (1): Immersion Exposure by ArF Excimer Laser, Development with Organic Solvent>

To a surface of a 12 inch silicon wafer was applied an underlayer antireflection film forming composition ("ARC66" manufactured by Brewer Science Incorporated.) by using a spin coater ("CLEAN TRACK ACT12" manufactured by Tokyo Electron Limited.). After applying, the wafer was heated at 205° C. for 60 seconds to form an underlayer antireflection film having a film thickness of 105 nm. Each radiation-sensitive resin composition was applied on the underlayer antireflection film by using the spin coater. The PAB (Post applied baking; baking after applying) was carried out at 100° C. for 50 seconds, and then cooled at 23° C. for 30 seconds to form a resist film having a film thickness of 90 nm. Next, the resist film was exposed through a mask pattern for forming a resist pattern having a hole of 58 nm and a pitch of 96 nm with an ArF excimer laser immersion exposure apparatus ("TWINSCAN XT-1900i" manufactured by ASML) in a optical condition of NA=1.35 and Annular (σ=0.8/0.6). After exposing, the PEB was carried out at 90° C. for 50 seconds. The resist film was subjected to a paddle development by using n-butyl acetate at 23° C. for 10 seconds. The resist film was spin dried at 2,000 rpm for 15 seconds with spinning off to form a resist pattern having a hole of 48 nm and a pitch of 96 nm. The exposed amount in which the size of the hole pattern was 48 nm during the formation of the resist pattern was regarded as optimum exposed amount (Eop).

<Formation of Resist Pattern (2): Immersion Exposure by ArF Excimer Laser, Alkaline Development>

To a surface of a 12 inch silicon wafer was applied an underlayer antireflection film forming composition ("ARC66" manufactured by Brewer Science Incorporated.) by using a spin coater ("CLEAN TRACK ACT12" manufactured by Tokyo Electron Limited.). After applying, the wafer was heated at 205° C. for 60 seconds to form an underlayer antireflection film having a film thickness of 105 nm. Each radiation-sensitive resin composition was applied on the underlayer antireflection film by using the spin coater. The PAB was carried out at 100° C. for 50 seconds, and then cooled at 23-C for 30 seconds to form a resist film having a film thickness of 90 nm. Next, the resist film was exposed through a mask pattern for forming a resist pattern having 38 nm line and space (1L/1S) with an ArF excimer laser immersion exposure apparatus ("TWINSCAN XT-1900i" manufactured by ASML) in a optical condition of NA=1.35 and Dipole35X (σ=0.97/0.77). After exposing, the PEB was carried out at 90° C. for 50 seconds. The resist film was subjected to a paddle development by using 2.38% by mass of aqueous TMAH solution at 23° C. for 30 seconds, and rinsed with ultrapure water for 7 seconds. The resist film was spin dried at 2,000 rpm for 15 seconds with spinning off to form a resist pattern having 40 nm line and space (1L/1S). During the formation of the resist pattern, the exposed amount in which the line was formed through a mask pattern for forming a pattern having 40 nm line and space (1L/1S) as the target size, and the width of the formed line was 40 nm was regarded as optimum exposed amount (Eop).

<Evaluation>

Using the formed resist patterns, each radiation-sensitive resin composition was evaluated by measuring according to the following method. The evaluation results are shown in the following Table 3. The scanning electron microscope ("CG-5000" manufactured by Hitachi High-Technologies Corporation) was used for measuring the length of the resist pattern.

[CDU Properties]

The hole pattern formed by exposing to the exposed amount as same as the Eop calculated in the Formation of Resist Pattern (1) was observed from the top of the pattern by using the scanning electron microscope. The hole diameter was measured at 16 points within a square 400 nm on a side, and the measurement values were averaged to determine the average value. The average value was measured at five hundred of arbitrary points. The 3σ value was calculated from the distribution of the measurement values, and the 3σ value was regarded as CDU properties (nm). The smaller the value is, the smaller the variation of the hole diameter over long period is, which is better. As the CDU properties, if the value was not more than 5.0 nm, it was evaluated as "good". If the value exceeded 5.0 nm, it was evaluated as "poor".

[MEEF Properties]

The hole pattern formed by exposing to the exposed amount as same as the Eop calculated in the Formation of Resist Pattern (1) was observed from the top of the pattern by using the scanning electron microscope. The hole diameter was measured at 16 points within a square 400 nm on a side, and the measurement values were averaged to determine the average value. The average value was measured at one hundred of arbitrary points. Similar measurement was each carried out in five conditions that the size of the mask was different by 1 nm. The amount of change in the hole diameter with respect to the amount of change in the mask was regarded as MEEF properties (nm). The smaller the value of the MEEF properties is, the better the mask fidelity is, which is better. As the MEEF properties, if the value was not more than 3.9 nm, it was evaluated as "good". If the value exceeded 3.9 nm, it was evaluated as "poor".

[LWR Properties]

The line and space pattern formed by exposing to the exposed amount as same as the Eop calculated in the Formation of Resist Pattern (2) was observed from the top of the pattern by using the scanning electron microscope. The variation of the line width was measuredat at five hundred points. The 3a value was calculated from the measurement values, and the 3a value was regarded as LWR properties (nm). The smaller the value of the LWR properties is, the smaller the wobble of the line is, which is better. As the LWR properties, if the value was not more than 3.9 nm, it was evaluated as "good". If the value exceeded 3.9 nm, it was evaluated as "poor".

TABLE 3

| | Radiation-sensitive resin composition | Development with organic solvent | | Alkaline development |
| --- | --- | --- | --- | --- |
| | | CDU (nm) | MEEF (nm) | LWR (nm) |
| Example 1 | J-1 | 4.0 | 3.2 | 2.9 |
| Example 2 | J-2 | 4.1 | 3.2 | 2.9 |
| Example 3 | J-3 | 4.0 | 3.1 | 2.8 |
| Example 4 | J-4 | 4.1 | 3.2 | 2.9 |
| Example 5 | J-5 | 4.3 | 3.3 | 3.0 |
| Example 6 | J-6 | 4.2 | 3.4 | 3.0 |
| Example 7 | J-7 | 4.4 | 3.4 | 3.2 |
| Example 8 | J-8 | 4.7 | 3.7 | 3.8 |
| Example 9 | J-9 | 4.7 | 3.7 | 3.8 |
| Example 10 | J-10 | 4.5 | 3.5 | 3.3 |
| Example 11 | J-11 | 4.2 | 3.2 | 3.0 |
| Example 12 | J-12 | 4.2 | 3.3 | 3.1 |
| Example 13 | J-13 | 4.3 | 3.4 | 3.5 |
| Example 14 | J-14 | 4.3 | 3.6 | 3.6 |
| Example 15 | J-15 | 4.1 | 3.6 | 3.5 |
| Example 16 | J-16 | 4.4 | 3.7 | 3.6 |
| Example 17 | J-17 | 4.5 | 3.5 | 3.4 |
| Example 18 | J-18 | 4.4 | 3.5 | 3.2 |
| Example 19 | J-19 | 4.5 | 3.6 | 3.5 |
| Example 20 | J-20 | 4.7 | 3.7 | 3.8 |
| Comparative example 1 | K-1 | 6.0 | 4.7 | 4.6 |
| Comparative example 2 | K-2 | 6.1 | 4.7 | 4.4 |
| Comparative example 3 | K-3 | 6.0 | 4.7 | 4.5 |
| Comparative example 4 | K-4 | 6.1 | 4.6 | 4.5 |
| Comparative example 5 | K-5 | 6.2 | 4.7 | 4.3 |
| Comparative example 6 | K-6 | 6.3 | 4.3 | 4.6 |
| Comparative example 7 | K-7 | 6.4 | 4.4 | 4.5 |

Example 21

The radiation-sensitive resin composition (J-21) was prepared by mixing 100 parts by mass of the base resin (A-2), 17 parts by mass of the compound (1-1) and 17 parts by mass of the compound (2-1) as the radiation-sensitive acid generator, 2.5 parts by mass of the compound (C-2) as the acid diffusion controlling agent, and 4,280 parts by mass of (E-1) and 1,830 parts by mass of (E-4) as the solvent, and then filtering through a membrane filter having a pore size of 0.2 m.

Examples 22-23 and Comparative Examples 8-10

The radiation-sensitive resin compositions (J-22) to (J-23) and (K-8) to (K-10) were prepared by using the method similar as in Example 21, except that the type and content of each ingredients as shown in Table 4 were used.

TABLE 4

| Radiation-sensitive resin composition | Base resin Type | Base resin Content (Parts by mass) | Radiation-sensitive acid generator Type | Radiation-sensitive acid generator Content (Parts by mass) | Radiation-sensitive acid generator Type | Radiation-sensitive acid generator Content (Parts by mass) | Acid diffusion controlling agent Type | Acid diffusion controlling agent Content (Parts by mass) | Solvent Type | Solvent Content (Parts by mass) |
|---|---|---|---|---|---|---|---|---|---|---|
| Example 21 | J-21 | A-2 | 100 | 1-1 | 17 | 2-1 | 17 | C-2 | 2.5 | E-1/E-4 | 4280/1830 |
| Example 22 | J-22 | A-2 | 100 | 1-1 | 17 | 2-2 | 17 | C-2 | 2.5 | E-1/E-4 | 4280/1830 |
| Example 23 | J-23 | A-2 | 100 | 1-1 | 17 | 2-3 | 17 | C-2 | 2.5 | E-1/E-4 | 4280/1830 |
| Comparative example 8 | K-8 | A-2 | 100 | 1-1 | 5 | 1-2 | 5 | C-3 | 2.5 | E-1/E-4 | 4280/1830 |
| Comparative example 9 | K-9 | A-2 | 100 | 2-1 | 5 | 2-6 | 5 | C-2 | 2.5 | E-1/E-4 | 4280/1830 |
| Comparative example 10 | K-10 | A-2 | 100 | 3-1 | 5 | 3-2 | 5 | C-2 | 2.5 | E-1/E-4 | 4280/1830 |

<Formation of Resist Pattern (3): Exposure with Electron Beam, Alkaline Development>

To a surface of a 8 inch silicon wafer was applied each radiation-sensitive resin composition as described in the above Table 4 by using a spin coater ("CLEAN TRACK ACT8" manufactured by Tokyo Electron Limited.). The PB was carried out at 90° C. for 60 seconds, and then cooled at 23° C. for 30 seconds to form a resist film having a film thickness of 50 nm. The resist film was exposed to an electron beam with a simplified model of Electron Beam Lithography Apparatus (manufactured by Hitachi, Ltd., model "HL800D", power output: 50 KeV, current density: 5.0 A/cm$^2$). After exposing, the PEB was carried out at 120° C. for 60 seconds. The resist film was developed by using 2.38% by mass of aqueous TMAH solution as the alkaline developing solution at 23° C. for 30 seconds, washed with water, and then dried to form a positive resist pattern having a hole of 100 nm and a pitch of 200 nm.

<Evaluation>

Using the formed resist patterns, the CDU properties of each radiation-sensitive resin composition was evaluated by exposing to the optimum exposed amount (Eop) according to the method as described above. The scanning electron microscope (S-9380 manufactured by Hitachi High-Technologies Corporation) was used for measuring the length of the resist pattern. The results are shown in the following Table 5.

TABLE 5

| Radiation-sensitive resin composition | | Alkaline development Eop (mJ) | Alkaline development CDU (nm) |
|---|---|---|---|
| Example 21 | J-21 | 33.0 | 2.9 |
| Example 22 | J-22 | 31.0 | 3.0 |
| Example 23 | J-23 | 32.0 | 3.1 |
| Comparative example 8 | K-8 | 40.0 | 4.6 |
| Comparative example 9 | K-9 | 33.0 | 4.7 |
| Comparative example 10 | K-10 | 35.0 | 4.8 |

As shown in Table 3 and Table 5, the radiation-sensitive resin compositions of Examples had good CDU properties, MEEF properties and LWR properties when the exposure with ArF was carried out. When the exposure with an electron beam was carried out, the compositions had good CDU properties. Therefore, the radiation-sensitive resin compositions are judged to have superior CDU properties, MEEF properties and LWR properties. In contrast, in the radiation-sensitive resin compositions of Comparative Examples, at least a part of these properties was poor. In general, it is known that in the exposure with an electron beam, the compositions show trends similar as in the EUV exposure. Therefore, it is expected that the radiation-sensitive resin compositions of Examples also has good CDU properties in EUV exposure.

INDUSTRIAL APPLICABILITY

According to the radiation-sensitive resin composition and the method for forming a resist pattern of the invention, the desired resist pattern can be formed having superior CDU properties, MEEF properties and LWR properties. Therefore, the composition and the method can be suitably used for producing a semiconductor device which is expected to be further micronized in the future.

What is claimed is:

1. A radiation-sensitive resin composition, comprising:
a base resin comprising a structure unit having an acid-dissociable group, a content of the structural unit in the base resin being 30-75 mol %;
a radiation-sensitive acid generator;
an acid diffusion controlling agent;
a fluorine-containing resin having a higher content by mass of fluorine atoms than the base resin; and
a solvent which is at least one solvent selected from the group consisting of iso-propanol, 4-methyl-2-pentanol, 3-methoxybutanol, n-hexanol, 2-ethylhexanol, furfuryl alcohol, cyclohexanol, 3,3,5-trimethylcyclohexanol, ethylene glycol, 1,2-propylene glycol, 2-methyl-2,4-pentanediol, 2,5-hexanediol, diethylene glycol, dipropylene glycol, triethylene glycol, tripropylene glycol, a partially etherized polyhydric alcohol-based solvent in which a part of hydroxy groups in the polyhydric alcohol is etherized, an ether-based solvent, acetone, butanone, methyl-iso-butyl ketone, cyclopentanone, cyclohexanone, methylcyclohexanone, 2,4-pentanedione, acetonylacetone, acetophenone, an amide-based solvent, an ester-based solvent, and a hydrocarbon-based solvent,
wherein the radiation-sensitive acid generator comprises:
a second compound which is at least one compound selected from the group consisting of a compound represented by formula (2-1), a compound represented by formula (2-2), a compound represented by formula (2-3), a compound represented by formula (2-4), a compound represented by formula (2-5), a compound represented by formula (2-6), a compound represented by formula (2-7), a compound represented by formula (2-8), a compound represented by formula (2-9), a compound represented by formula (2-10), a compound represented by formula (2-11), and a compound represented by formula (2-12);

a third compound which is at least one compound selected from the group consisting of a compound represented by formula (3-1), a compound represented by formula (3-2), a compound represented by formula (3-3), a compound represented by formula (3-4), a compound represented by formula (3-5), a compound represented by formula (3-6), a compound represented by formula (3-7), a compound represented by formula (3-8), a compound represented by formula (3-9), a compound represented by formula (3-10), and a compound represented by formula (3-11); and optionally, a first compound represented by formula (1):

(2-1)
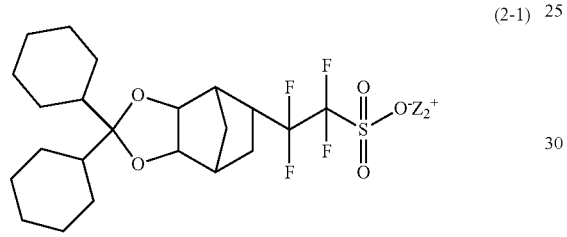

(2-2)
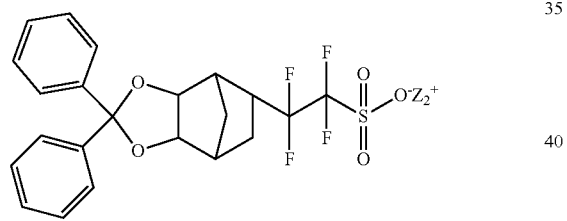

(2-3)
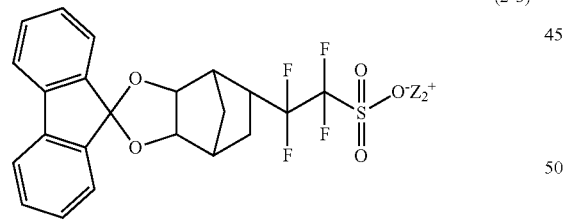

(2-4)
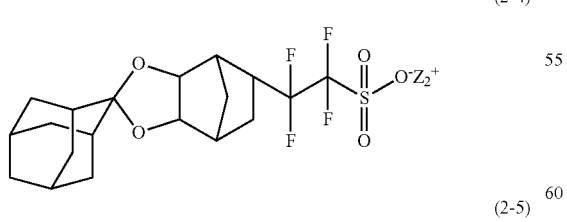

(2-5)
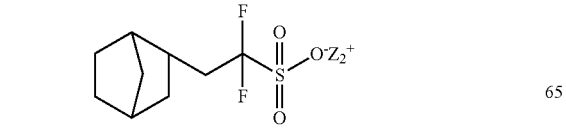

(2-6)
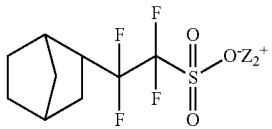

(2-7)
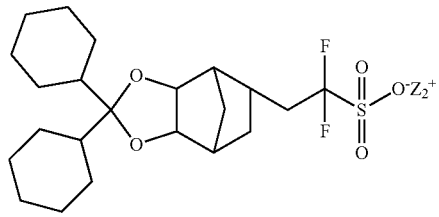

(2-8)
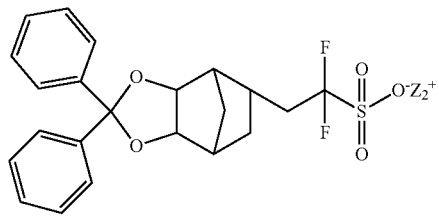

(2-9)
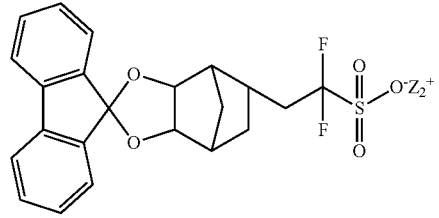

(2-10)
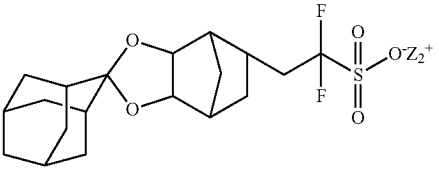

(2-11)
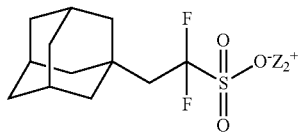

(2-12)
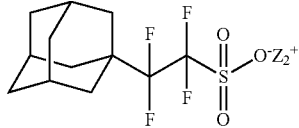

(3-1)
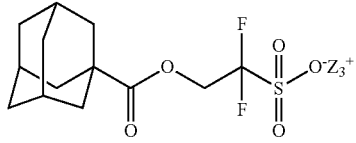

-continued (3-2) 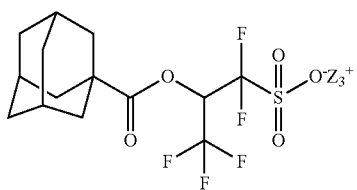

(3-3) 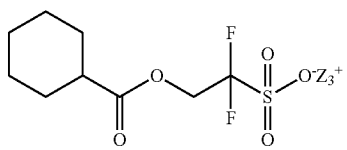

(3-4) 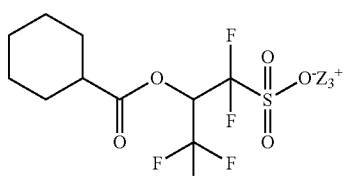

(3-5) 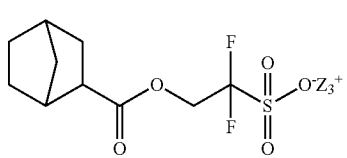

(3-6) 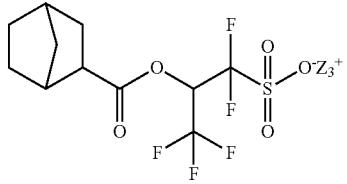

(3-7) 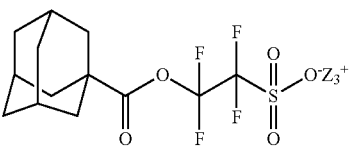

(3-8) 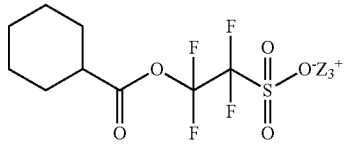

(3-9) 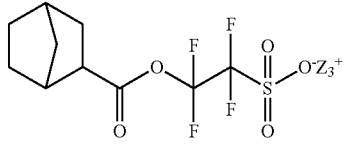

(3-10) 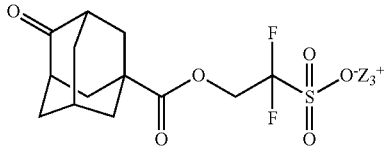

(3-11) 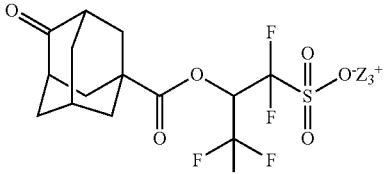

(1) 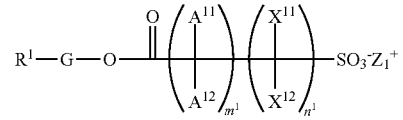

wherein:

$R^1$ is a group having a cyclic structure;

$X^{11}$ and $X^{12}$ are each independently a hydrogen atom, a fluorine atom, or a fluorinated hydrocarbon group, provided that at least one of $X^{11}$ and $X^{12}$ is not a hydrogen atom;

$A^{11}$ and $A^{12}$ are each independently a hydrogen atom, or a hydrocarbon group having a carbon number of 1 to 20;

$m^1$ is an integer of 0 to 5;

$n^1$ is an integer of 1 to 4;

G is a single bond, or a divalent linking group; and $Z_1^+$, $Z_2^+$ and $Z_3^+$ are each independently a monovalent onium cation, wherein an amount of the radiation-sensitive acid generator is from 7 to 35 mass parts with respect to 100 mass parts of the base resin, an amount of the acid diffusion controlling agent is from 5 to 110 mass parts with respect to 100 mass parts of the radiation-sensitive acid generator, and an amount of the fluorine-containing resin is from 1 to 5 mass parts with respect to 100 mass parts of the base resin.

2. The radiation-sensitive resin composition according to claim 1, wherein the radiation-sensitive acid generator comprises the first compound, and a total content of the first compound is not less than 1 part by mass and not more than 45 parts by mass based on 100 parts by mass of the base resin.

3. The radiation-sensitive resin composition according to claim 1, wherein a molecular weight of an anionic moiety in the radiation-sensitive acid generator is 230 or more.

4. A method of forming a resist pattern, comprising:

forming a resist film from the radiation-sensitive resin composition according to claim 1;

exposing the resist film; and developing the exposed resist film.

5. The radiation-sensitive resin composition according to claim 1, wherein the acid diffusion controlling agent is an onium salt compound wherein the onium salt compound is degraded and loses acid diffusion controlling properties by an exposure.

6. The radiation-sensitive resin composition according to claim 5, wherein the onium salt compound is triphenylsulfonium salicylate or triphenylsulfonium 10-camphorsulfonate.

7. The radiation-sensitive resin composition according to claim 1,
wherein $Z_1^+$, $Z_2^+$, and $Z_3^+$ are each independently represented by formula (X-1):

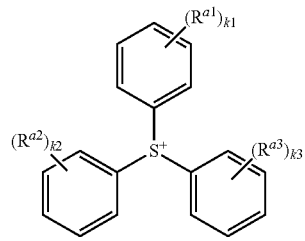

(X-1)

wherein:
k1, k2 and k3 are each independently an integer of 0 to 5; and
$R^{a1}$, $R^{a2}$ and $R^{a3}$ are each independently, at each occurrence, a substituted or unsubstituted, straight or branched chain alkyl group, alkoxy group or alkoxycarbonyloxy group having a carbon number of 1 to 12; a substituted or unsubstituted, monocyclic or polycyclic cycloalkyl group having a carbon number of 3 to 12; a substituted or unsubstituted aromatic hydrocarbon group having a carbon number of 6 to 12; a hydroxy group; —OSO₂—$R^P$; —SO₂—$R^Q$; or —S—$R^T$, wherein $R^P$, $R^Q$ and $R^T$ are each independently, at each occurrence, a substituted or unsubstituted, straight or branched chain alkyl group having a carbon number of 1 to 12; a substituted or unsubstituted alicyclic hydrocarbon group having a carbon number of 5 to 25; or a substituted or unsubstituted aromatic hydrocarbon group having a carbon number of 6 to 12.

8. The radiation-sensitive resin composition according to claim 1, wherein the monovalent onium cation represented by $Z_1^+$, $Z_2^+$ and $Z_3^+$ is an unsubstituted triphenylsulfonium.

9. The method according to claim 4, wherein the radiation-sensitive acid generator comprises the first compound, and a total content of the first compound is not less than 1 part by mass and not more than 45 parts by mass based on 100 parts by mass of the base resin.

10. The method according to claim 4, wherein a molecular weight of an anionic moiety in the radiation-sensitive acid generator is 230 or more.

11. The method according to claim 4, wherein the acid diffusion controlling agent is an onium salt compound wherein the onium salt compound is degraded and loses acid diffusion controlling properties by an exposure.

12. The method according to claim 11, wherein the onium salt compound is triphenylsulfonium salicylate or triphenylsulfonium 10-camphorsulfonate.

13. The method according to claim 4,
wherein $Z_1^+$, $Z_2^+$, and $Z_3^+$ are each independently represented by formula (X-1):

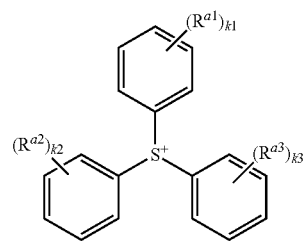

(X-1)

wherein:
k1, k2 and k3 are each independently an integer of 0 to 5; and
$R^{a1}$, $R^{a2}$ and $R^{a3}$ are each independently, at each occurrence, a substituted or unsubstituted, straight or branched chain alkyl group, alkoxy group or alkoxycarbonyloxy group having a carbon number of 1 to 12; a substituted or unsubstituted, monocyclic or polycyclic cycloalkyl group having a carbon number of 3 to 12; a substituted or unsubstituted aromatic hydrocarbon group having a carbon number of 6 to 12; a hydroxy group; —OSO₂—$R^P$; —SO₂—$R^Q$; or —S—$R^T$, wherein $R^P$, $R^Q$ and $R^T$ are each independently, at each occurrence, a substituted or unsubstituted, straight or branched chain alkyl group having a carbon number of 1 to 12; a substituted or unsubstituted alicyclic hydrocarbon group having a carbon number of 5 to 25; or a substituted or unsubstituted aromatic hydrocarbon group having a carbon number of 6 to 12.

14. The method according to claim 4, wherein the monovalent onium cation represented by $Z_1^+$, $Z_2^+$ and $Z_3^+$ is an unsubstituted triphenylsulfonium.

15. A radiation-sensitive resin composition, comprising:
a resin comprising a structure unit having an acid-dissociable group, a content of the structural unit in the base resin being 30-75 mol %;
a radiation-sensitive acid generator;
an acid diffusion controlling agent;
a fluorine-containing resin having higher content by mass of fluorine atoms than the base resin; and
a solvent which is at least one solvent selected from the group consisting of iso-propanol, 4-methyl-2-pentanol, 3-methoxybutanol, n-hexanol, 2-ethylhexanol, furfuryl alcohol, cyclohexanol, 3,3,5-trimethylcyclohexanol, ethylene glycol, 1,2-propylene glycol, 2-methyl-2,4-pentanediol, 2,5-hexanediol, diethylene glycol, dipropylene glycol, triethylene glycol, tripropylene glycol, a partially etherized polyhydric alcohol-based solvent in which a part of hydroxy groups in the polyhydric alcohol is etherized, an ether-based solvent, acetone, butanone, methyl-iso-butyl ketone, cyclopentanone, cyclohexanone, methylcyclohexanone, 2,4-pentanedione, acetonylacetone, acetophenone, an amide-based solvent, an ester-based solvent, and a hydrocarbon-based solvent,
wherein the radiation-sensitive acid generator comprises:
a second compound which is at least one compound selected from the group consisting of a compound represented by formula (2-1), a compound represented by formula (2-2), a compound represented by formula (2-3), a compound represented by formula (2-4), a compound represented by formula (2-5), a compound represented by formula (2-7), a compound represented by formula (2-8), a compound represented by formula (2-9), a compound represented by formula (2-10), and a compound represented by formula (2-12);

a third compound which is at least one compound selected from the group consisting of a compound represented by formula (3-3), a compound represented by formula (3-5), a compound represented by formula (3-7), a compound represented by formula (3-8), a compound represented by formula (3-9), and a compound represented by formula (3-10); and optionally, a first compound represented by formula (1):

(2-1)
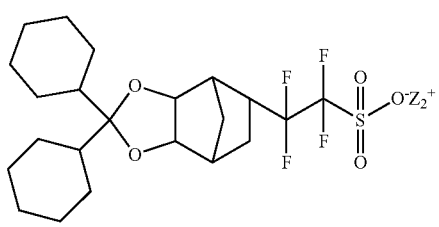

(2-2)
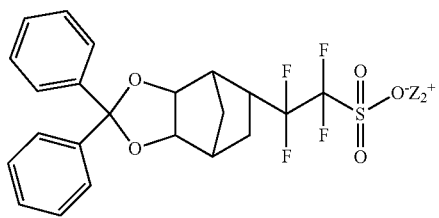

(2-3)
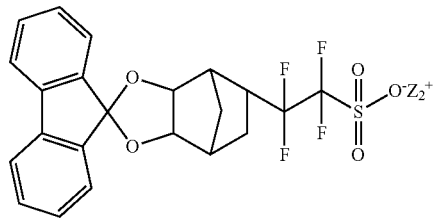

(2-4)
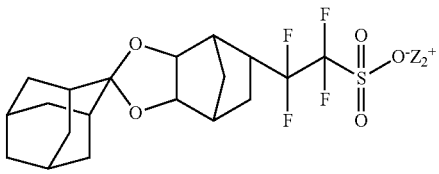

(2-5)
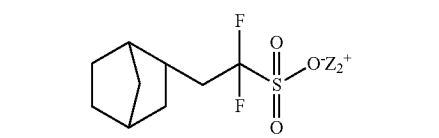

(2-7)
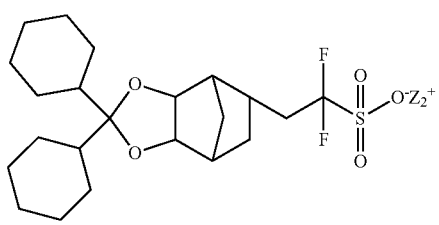

-continued (2-8)
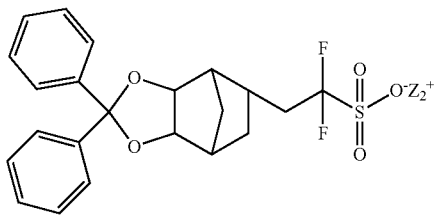

(2-9)
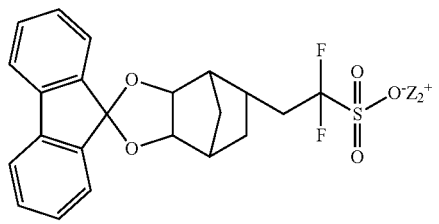

(2-10)
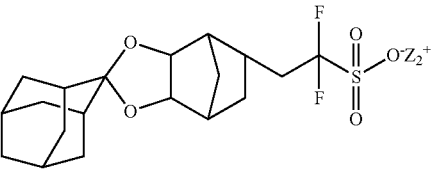

(2-12)
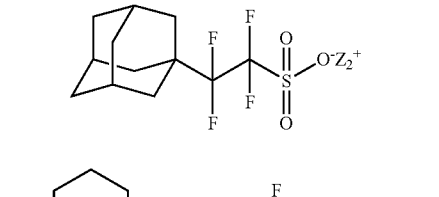

(3-3)
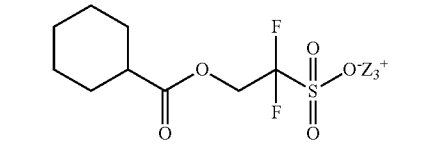

(3-5)
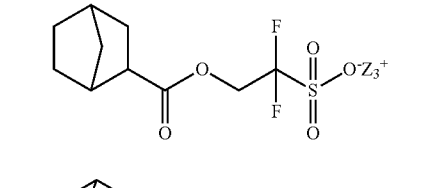

(3-7)
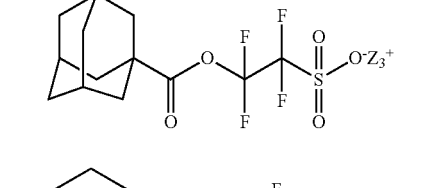

(3-8)
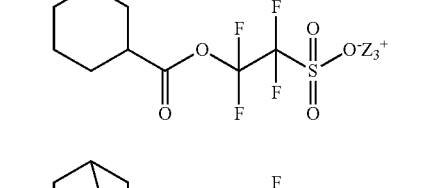

(3-9)
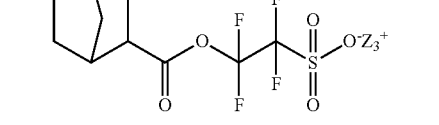

-continued (3-10)

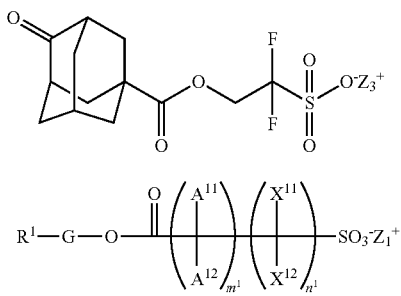

(1)

$$R^1-G-O-\overset{O}{\overset{\|}{C}}-\left(\overset{A^{11}}{\underset{A^{12}}{|}}\right)_{m^1}\left(\overset{X^{11}}{\underset{X^{12}}{|}}\right)_{n^1}-SO_3^-Z_1^+$$

wherein:
$R^1$ is a group having a cyclic structure;
$X^{11}$ and $X^{12}$ are each independently a hydrogen atom, a fluorine atom, or a fluorinated hydrocarbon group, provided that at least one of $X^{11}$ and $X^{12}$ is not a hydrogen atom, and at least one of $X^{21}$ and $X^{22}$ is not a hydrogen atom;
$A^{11}$ and $A^{12}$ are each independently a hydrogen atom, or a hydrocarbon group having a carbon number of 1 to 20;
$m^1$ is an integer of 0 to 5;
$n^1$ is an integer of 1 to 4;
G is a single bond, or a divalent linking group; and
$Z_1^+$, $Z_2^+$ and $Z_3^+$ are each independently a monovalent onium cation,
wherein
an amount of the radiation-sensitive acid generator is from 7 to 35 mass parts with respect to 100 mass parts of the base resin,
an amount of the acid diffusion controlling agent is from 5 to 110 mass parts with respect to 100 mass parts of the radiation-sensitive acid generator, and
an amount of the fluorine-containing resin is from 1 to 5 mass parts with respect to 100 mass parts of the base resin.

16. The radiation-sensitive resin composition according to claim 1, wherein an amount of the second compound is 5 mass parts or more with respect to 100 mass parts of the base resin, and an amount of the third compound is 5 mass parts or more with respect to 100 mass parts of the base resin.

17. The radiation-sensitive resin composition according to claim 1, wherein the amount of the acid diffusion controlling agent is from 4 to 7 mass parts with respect to 100 mass parts of the base resin.

18. The radiation-sensitive resin composition according to claim 1, wherein the radiation-sensitive resin composition consists of: the base resin; the radiation-sensitive acid generator; the acid diffusion control agent; the fluorine-containing resin; optionally a surfactant; and optionally a sensitizer.

19. The radiation-sensitive resin composition according to claim 1, wherein an amount of the second compound is 5 mass parts or more with respect to 100 mass parts of the base resin, an amount of the third compound is 5 mass parts or more with respect to 100 mass parts of the base resin, and the amount of the acid diffusion controlling agent is from 4 to 7 mass parts with respect to 100 mass parts of the base resin.

20. The radiation-sensitive resin composition according to claim 15, wherein an amount of the second compound is 5 mass parts or more with respect to 100 mass parts of the base resin, an amount of the third compound is 5 mass parts or more with respect to 100 mass parts of the base resin, and the amount of the acid diffusion controlling agent is from 4 to 7 mass parts with respect to 100 mass parts of the base resin.

* * * * *